US012753323B2

(12) United States Patent
Takashita

(10) Patent No.: US 12,753,323 B2
(45) Date of Patent: Oct. 6, 2026

(54) FLUORINE-CONTAINING ETHER COMPOUND, SURFACE TREATMENT AGENT, FLUORINE-CONTAINING ETHER COMPOSITION, COATING LIQUID, ARTICLE, AND COMPOUND

(71) Applicant: AGC Inc., Tokyo (JP)

(72) Inventor: Ryuta Takashita, Chiyoda-ku (JP)

(73) Assignee: AGC Inc., Tokyo (JP)

( * ) Notice: Subject to any disclaimer, the term of this patent is extended or adjusted under 35 U.S.C. 154(b) by 1117 days.

(21) Appl. No.: 17/655,224

(22) Filed: Mar. 17, 2022

(65) Prior Publication Data

US 2022/0213345 A1 Jul. 7, 2022

Related U.S. Application Data

(63) Continuation of application No. PCT/JP2020/035358, filed on Sep. 17, 2020.

(30) Foreign Application Priority Data

Sep. 20, 2019 (JP) ................................ 2019-171550

(51) Int. Cl.

| | |
|---|---|
| ***C09D 171/02*** | (2006.01) |
| ***C03C 17/30*** | (2006.01) |
| ***C07C 21/215*** | (2006.01) |
| ***C07C 33/02*** | (2006.01) |
| ***C07C 69/587*** | (2006.01) |
| ***C07F 3/02*** | (2006.01) |
| ***C08G 65/336*** | (2006.01) |
| ***C09D 5/00*** | (2006.01) |

(52) U.S. Cl.

CPC ............ *C09D 171/02* (2013.01); *C03C 17/30* (2013.01); *C07C 21/215* (2013.01); *C07C 33/02* (2013.01); *C07C 69/587* (2013.01); *C07F 3/02* (2013.01); *C08G 65/336* (2013.01); *C09D 5/00* (2013.01); *C03C 2217/76* (2013.01); *C03C 2217/78* (2013.01); *C03C 2218/151* (2013.01)

(58) Field of Classification Search

CPC ...... C07F 7/14; C07F 7/16; C07F 7/20; C07F 3/02; C09D 171/02; C09D 5/00; C03C 17/30; C03C 2217/76; C03C 2217/78; C03C 2218/151; C07C 21/215; C07C 33/02; C07C 69/587; C08G 65/336

See application file for complete search history.

(56) References Cited

U.S. PATENT DOCUMENTS 5,759,629 A * 6/1998 van Ooij .................. C09D 4/00 427/409
6,127,498 A 10/2000 Tonelli et al.
6,183,872 B1 2/2001 Tanaka et al.
6,200,684 B1 3/2001 Yamaguchi et al.
10,450,413 B2 * 10/2019 Mitsuhashi ............. C03C 17/30
2004/0259991 A1 * 12/2004 Cai ....................... C08L 51/085 524/556
2010/0129672 A1 5/2010 Hao et al.
2012/0077041 A1 3/2012 Yamane et al.
2014/0287240 A1 9/2014 Murotani et al.
2014/0287246 A1 9/2014 Murotani et al.
2014/0302332 A1 10/2014 Murotani et al.
2015/0274889 A1 10/2015 Sakoh et al.
2015/0307719 A1 10/2015 Mitsuhashi et al.
2015/0315443 A1 11/2015 Takeda et al.
2016/0009929 A1 1/2016 Hoshino et al.
2016/0040039 A1 2/2016 Yamane et al.
2016/0264788 A1 9/2016 Hoshino et al.
2016/0304665 A1 10/2016 Sakoh et al.
2016/0319071 A1 11/2016 Sakoh et al.
2016/0355638 A1 12/2016 Sakoh et al.
2018/0142062 A1 5/2018 Hoshino et al.
2018/0148606 A1 * 5/2018 Hoshino .............. C08G 65/329

(Continued)

FOREIGN PATENT DOCUMENTS

CN 108440593 A * 8/2018 ........... C09D 5/1675
EP 0 933 377 A2 8/1999

(Continued)

OTHER PUBLICATIONS

Agilent, Polymer Molecular Weight Distribution and Definitions of MW Averages, pp. 1-4 (2015) (Year: 2015).*

(Continued)

*Primary Examiner* — Alexander R Pagano

(74) *Attorney, Agent, or Firm* — Oblon, McClelland, Maier & Neustadt, L.L.P.

(57) ABSTRACT

Provided are a fluorine-containing ether compound, fluorine-containing ether composition and coating liquid that can form a surface layer having excellent durability, an article having a surface layer that has excellent durability, and a compound that is useful as a raw material of a fluorine-containing ether compound. The fluorine-containing ether compound is represented by the following formula (A1) or formula (A2):

Formula (A1)

$$R^f—O—(R^{f1}O)_m—R^{f2}[—R^1—C(—R^2—T)_a(—R^3)_{3-a}]_b$$

Formula (A2)

$$[(T\text{-}R^2—)_a(R^3—)_{3-a}C—R^1—]_bR^{f2}—O——(R^{f1}O)_m—R^{f2}[—R^1—C(—R^2—T)_a(—R^3)_{3-a}]_b$$

wherein each of the reference signs in the formulas are as described in the specification.

10 Claims, No Drawings

(56) References Cited

U.S. PATENT DOCUMENTS

| | | | | |
|---|---|---|---|---|
| 2019/0002635 | A1 | 1/2019 | Mitsuhashi et al. | |
| 2019/0040266 | A1 | 2/2019 | Hoshino et al. | |
| 2019/0177574 | A1* | 6/2019 | Takeda | C08G 77/54 |
| 2020/0002551 | A1* | 1/2020 | Mitsuhashi | C09D 183/12 |
| 2020/0002567 | A1* | 1/2020 | Mitsuhashi | C09D 5/00 |
| 2020/0056067 | A1* | 2/2020 | Mitsuhashi | C08G 65/007 |
| 2020/0071251 | A1* | 3/2020 | Hoshino | C07F 7/1804 |
| 2020/0083456 | A1 | 3/2020 | Sugioka et al. | |
| 2020/0157376 | A1 | 5/2020 | Hoshino et al. | |
| 2020/0165273 | A1 | 5/2020 | Hoshino et al. | |
| 2020/0165384 | A1 | 5/2020 | Hoshino et al. | |
| 2020/0165385 | A1 | 5/2020 | Uno et al. | |
| 2020/0231747 | A1 | 7/2020 | Furukawa et al. | |
| 2020/0354520 | A1* | 11/2020 | Mitsuhashi | C08G 65/336 |
| 2022/0204444 | A1* | 6/2022 | Takashita | C07C 17/2632 |
| 2023/0024292 | A1* | 1/2023 | Takashita | C09D 5/1662 |

FOREIGN PATENT DOCUMENTS

| | | | | | |
|---|---|---|---|---|---|
| JP | 61-18901 | A | | 1/1986 | |
| JP | 07-278547 | A | | 10/1995 | |
| JP | H07278547 | A | * | 10/1995 | |
| JP | 11-029585 | A | | 2/1999 | |
| JP | 2874715 | B2 | | 3/1999 | |
| JP | 2000-144097 | A | | 5/2000 | |
| JP | 2000-327772 | A | | 11/2000 | |
| JP | 2002-506887 | A | | 3/2002 | |
| JP | 2008-534696 | A | | 8/2008 | |
| JP | 4138936 | B2 | | 8/2008 | |
| JP | 2012-072272 | A | | 4/2012 | |
| JP | 2014-070163 | A | | 4/2014 | |
| JP | 2014-080473 | A | | 5/2014 | |
| JP | 2014-218639 | A | | 11/2014 | |
| JP | 2015-199906 | A | | 11/2015 | |
| JP | 2016-037541 | A | | 3/2016 | |
| JP | 2016-204656 | A | | 12/2016 | |
| JP | 2016-210854 | A | | 12/2016 | |
| JP | 2016-222859 | A | | 12/2016 | |
| JP | 2019-044158 | A | | 3/2019 | |
| JP | 6501016 | B1 | | 4/2019 | |
| JP | 2019-070100 | A | | 5/2019 | |
| KR | 10-2019-0104614 | A | | 9/2019 | |
| WO | WO 99/037720 | A1 | | 7/1999 | |
| WO | WO-2004000851 | A2 | * | 12/2003 | C07F 7/0874 |
| WO | WO 2006/107083 | A2 | | 10/2006 | |
| WO | WO 2011/059430 | A1 | | 5/2011 | |
| WO | WO 2011/060047 | A1 | | 5/2011 | |
| WO | WO 2012/064649 | A1 | | 5/2012 | |
| WO | WO 2013/042732 | A1 | | 3/2013 | |
| WO | WO 2013/121984 | A1 | | 8/2013 | |
| WO | WO 2013/121985 | A1 | | 8/2013 | |
| WO | WO 2013/121986 | A1 | | 8/2013 | |
| WO | WO 2014/126064 | A1 | | 8/2014 | |
| WO | WO 2014/163004 | A1 | | 10/2014 | |
| WO | WO 2015/087902 | A1 | | 6/2015 | |
| WO | WO-2017022437 | A1 | * | 2/2017 | C07F 7/18 |
| WO | WO 2017/038830 | A1 | | 3/2017 | |
| WO | WO 2017/038832 | A1 | | 3/2017 | |
| WO | WO 2017/187775 | A1 | | 11/2017 | |
| WO | WO-2018034138 | A1 | * | 2/2018 | C08G 65/336 |
| WO | WO 2018/079743 | A1 | | 5/2018 | |
| WO | WO 2018/143433 | A1 | | 8/2018 | |
| WO | WO 2018/146779 | A1 | | 8/2018 | |
| WO | WO-2018151055 | A1 | * | 8/2018 | C08L 71/00 |
| WO | WO 2018/216630 | A1 | | 11/2018 | |
| WO | WO 2019/039186 | A1 | | 2/2019 | |
| WO | WO 2019/039226 | A1 | | 2/2019 | |
| WO | WO 2019/039341 | A1 | | 2/2019 | |
| WO | WO 2019/044479 | A1 | | 3/2019 | |
| WO | WO-2019049753 | A1 | * | 3/2019 | C09K 3/18 |
| WO | WO-2019049754 | A1 | * | 3/2019 | C09K 3/18 |
| WO | WO 2019/163282 | A1 | | 8/2019 | |
| WO | WO-2020071330 | A1 | * | 4/2020 | C08L 71/02 |

OTHER PUBLICATIONS

W. Sheu, 78 Journal of Chemical Education, 554-555 (2001) (Year: 2001).*

Smrcek, J. et al., "Total syntheses of all tri-oxygenated 16-phytoprostane classes via a common precursor constructed by oxidative cyclization and alkyl-alkyl coupling reactions as the key steps," Organic & Biomolecular Chemistry, vol. 15, No. 44, 2017, XP093123760, pp. 9408-9414.

International Search Report issued Dec. 1, 2020 in PCT/JP2020/035358 filed on Sep. 17, 2020, 2 pages.

Krech et al., "Intramolecular Hydrostannation—Cyclic and Bicyclic Stannanes", Zeitschrift fuer Anorganische und Allgemeine Chemie, 1988, vol. 557, pp. 143-152.

* cited by examiner

FLUORINE-CONTAINING ETHER COMPOUND, SURFACE TREATMENT AGENT, FLUORINE-CONTAINING ETHER COMPOSITION, COATING LIQUID, ARTICLE, AND COMPOUND

INCORPORATION BY REFERENCE

This application is based upon and claims the benefit of priority from Japanese Patent Application 2019-171550 filed on Sep. 20, 2019, and PCT application No. PCT/JP2020/035358 filed on Sep. 17, 2020, the disclosure of which is incorporated herein in its entirety by reference.

BACKGROUND

The present invention relates to a fluorine-containing ether compound, a surface treatment agent, a fluorine-containing ether composition, a coating liquid, an article, and a compound.

Fluorine-containing ether compounds having a perfluoropolyether chain and a hydrolyzable silyl group can form a surface layer exhibiting high lubricity, water and oil repellency, and the like on the surface of a substrate, and therefore are suitably used for a surface treatment agent. Surface treatment agents including a fluorine-containing ether compound are used as a surface treatment agent in applications requiring the long-term maintenance of a performance (abrasion resistance) in which water and oil repellency is not likely to deteriorate even when a surface layer is repeatedly rubbed by a finger and a performance (fingerprint stain removability) capable of removing a fingerprint adhered to the surface layer easily by wiping off, for example, a member constituting a surface of a touch panel to be touched by fingers, a spectacle lens, and a display of a wearable terminal.

As a fluorine-containing ether compound capable of forming a surface layer having excellent abrasion resistance and fingerprint stain removability on the surface of substrate, fluorine-containing ether compounds having a perfluoropolyether chain and a hydrolyzable silyl group have been proposed (Japanese Unexamined Patent Application Publication No. 2016-037541; WO2017/022437; WO 2017/038830)

SUMMARY

The above-described surface treatment agent may be used not only for treating the surface of a display face of a smartphone, a tablet terminal, or the like, but also for treating the surface on the back side of a mobile device (the surface opposite to the display screen). Further improvement in the durability of the surface treatment agent is required.

An object of the present invention is to provide a fluorine-containing ether compound that can form a surface layer having excellent durability, a surface treatment agent, fluorine-containing ether composition and coating liquid that comprise the fluorine-containing ether compound, an article having a surface layer that has excellent durability, and a compound that is useful as a raw material of a fluorine-containing ether compound.

The present invention provides a fluorine-containing ether compound, a surface treatment agent, a fluorine-containing ether composition, a coating liquid, an article, and a raw material compound of a fluorine-containing compound, which have the configuration of the following [1] to [13].

[1] A fluorine-containing ether compound represented by the following formula (A1) or formula (A2):

$$R^f—O—(R^{f1}O)_m—R^{f2}[—R^1—C(—R^2—T)_a(—R^3)_{3-a}]_b \quad \text{Formula (A1)}$$

$$[(T\text{-}R^2—)_a(R^3—)_{3-a}C—R^1—]_bR^{f2}—O—(R^{f1}O)_m—R^{f2}[—R^1—C(—R^2—T)_a(—R^3)_{3-a}]_b \quad \text{Formula (A2)}$$

wherein $R^f$ is a fluoroalkyl group having 1 to 20 carbon atoms, $R^{f1}$ is a fluoroalkylene group having 1 to 6 carbon atoms, $R^{f2}$ is an organic group having a valence of (1+b), where at least a carbon atom bonded to $R^1$ bonds to a fluorine atom, and when there is a plurality of $R^{f2}$, the $R^{f2}$ may be the same or different, $R^1$ is an alkylene group having 1 to 20 carbon atoms, and when there is a plurality of the $R^1$ may be the same or different, $R^2$ is an alkylene group having 2 to 10 carbon atoms and optionally a fluorine atom, and a plurality of $R^2$ may be the same or different, $R^3$ is a hydrogen atom or an alkyl group having 1 to 10 carbon atoms and optionally a fluorine atom, and when there is a plurality of $R^3$, the plurality of $R^3$ may be the same or different, T is $—Si(R)_{3-c}(L)_c$, and a plurality of T may be the same or different, R is an alkyl group, L is a hydrolytic group or a hydroxyl group, and 2 or more L in T may be the same or different, m is an integer from 1 to 20, a is an integer from 1 to 3, and when there is a plurality of a, the plurality of a may be the same or different, b is an integer of 1 or more, and when there is a plurality of b, the plurality of b may be the same or different, c is 2 or 3, and a plurality of c may be the same or different, and when b is 1, a is 2 or 3.

[2] The fluorine-containing ether compound of [1], wherein all of the plurality of $R^2$ have 3 or more carbon atoms.

[3] The fluorine-containing ether compound of [1] or [2], wherein $R^1$ has from 5 to 20 carbon atoms.

[4] The fluorine-containing ether compound of [1] to [3], wherein the number of $—CH_2—$ is from 8 to 30.

[5] The fluorine-containing ether compound of [1] to [4], wherein weight average molecular weight (Mw)/number average molecular weight (Mn) is 1.2 or less.

[6] The fluorine-containing ether compound of [1] to [5], wherein the hydrolytic group is an alkoxy group, an aryloxy group, a halogen atom, an acyl group, an acyloxy group, or an isocyanate group.

[7] A surface treatment agent comprising the compound of any one of [1] to [6].

[8] A fluorine-containing ether composition comprising:

a fluorine-containing ether compound represented by the following formula (A1); and a fluorine-containing ether compound represented by the following formula (A2):

Formula (A1)

$$R^f—O—(R^{f1}O)_m—R^{f2}[—R^1—C(—R^2—T)_a(—R^3)_{3-a}]_b$$

Formula (A2)

$$[(T\text{-}R^2—)_a(R^3—)_{3-a}C—R^1—]_bR^{f2}—O—(R^{f1}O)_m—R^{f2}[—R^1—C(—R^2—T)_a(—R^3)_{3-a}]_b$$

wherein $R^f$ is a fluoroalkyl group having 1 to 20 carbon atoms, $R^{f1}$ is a fluoroalkylene group having 1 to 6 carbon atoms, $R^{f2}$ is an organic group having a valence of (1+b), where at least a carbon atom bonded to $R^1$ bonds to a fluorine atom, and when there is a plurality of $R^{f2}$, the $R^{f2}$ may be the same or different, $R^1$ is an alkylene group having 1 to 20 carbon atoms, and when there is a plurality of $R^1$, the $R^1$ may be the same or different, $R^2$ is an alkylene group having 2 to 10 carbon atoms and optionally a fluorine atom, and a plurality of $R^2$ may be the same or different, $R^3$ is a hydrogen atom or an alkyl group having 1 to 10 carbon atoms and optionally a fluorine atom, and when there is a plurality of $R^3$, the plurality of $R^3$ may be the same or different, T is —$Si(R)_{3-c}(L)_c$, and a plurality of T may be the same or different, R is an alkyl group, L is a hydrolytic group or a hydroxyl group, and 2 or more L in T may be the same or different, m is an integer from 1 to 20, a is an integer from 1 to 3, and when there is a plurality of a, the plurality of a may be the same or different, b is an integer of 1 or more, and when there is a plurality of b, the plurality of b may be the same or different, c is 2 or 3, and a plurality of c may be the same or different, and when b is 1, a is 2 or 3.

[9] A fluorine-containing ether composition comprising:

one or more of the fluorine-containing ether compound of [1] to [6]; and an additional fluorine-containing ether compound.

[10] A coating liquid comprising:

the fluorine-containing ether compound of [1] to [6] or the fluorine-containing ether composition of [8] or [9]; and a liquid medium.

[11] An article comprising a surface layer formed from the fluorine-containing ether compound of [1] to [6] or the fluorine-containing ether composition of [8] or [9] on a surface of a substrate.

[12] A compound represented by the following formula (B1):

Formula (B1)

$$(CH_2═CH—R^{20}—)_a(R^3—)_{3-a}C—R^{21}—X$$

wherein $R^{20}$ is a single bond or an alkylene group having 1 to 8 carbon atoms and optionally a fluorine atom, and when there is a plurality of $R^{20}$, the plurality of $R^{20}$ may be the same or different, $R^{21}$ is a single bond or an alkylene group having 1 to 19 carbon atoms, $R^3$ is a hydrogen atom or an alkyl group having 1 to 10 carbon atoms and optionally a fluorine atom, and when there is a plurality of $R^3$, the plurality of $R^3$ may be the same or different, X is a chlorine atom, a bromine atom, or an iodine atom, and a is an integer from 1 to 3.

[13] A compound represented by the following formula (B2):

Formula (B2)

$$(CH_2═CH—R^{20}—)_a(R^3—)_{3-a}C—R^{21}—MgX$$

wherein $R^{20}$ is a single bond or an alkylene group having 1 to 8 carbon atoms and optionally a fluorine atom, and when there is a plurality of $R^{20}$, the plurality of $R^{20}$ may be the same or different, $R^{21}$ is a single bond or an alkylene group having 1 to 19 carbon atoms, $R^3$ is a hydrogen atom or an alkyl group having 1 to 10 carbon atoms and optionally a fluorine atom, and when there is a plurality of $R^3$, the plurality of $R^3$ may be the same or different, X is a chlorine atom, a bromine atom, or an iodine atom, and a is an integer from 1 to 3.

The above and other objects, features and advantages of the present disclosure will become more fully understood from the detailed description given hereinbelow and the accompanying drawings which are given by way of illustration only, and thus are not to be considered as limiting the present disclosure.

DESCRIPTION OF EMBODIMENTS

The present invention provides a fluorine-containing ether compound that can form a surface layer having excellent durability, a surface treatment agent, fluorine-containing ether composition and coating liquid that include the fluorine-containing ether compound, an article having a surface layer that has excellent durability, and a compound that is useful as a raw material of a fluorine-containing ether compound.

In the present specification, the compound represented by formula (A1) is written as the "compound (A1)." Compounds and the like represented by other formulas are also written in this way.

The meaning of the following terms in the present specification are as follows.

"Reactive silyl group" is a generic term for hydrolyzable silyl groups and silanol groups (Si—OH). The reactive silyl group is, for example, T in formula (A1) or formula (A2), that is, —$Si(R)_{3-c}(L)_c$.

"Hydrolyzable silyl group" means a group that can hydrolyze to form a silanol group.

"Surface layer" means a layer formed at the surface of a substrate.

If the fluorine-containing ether compound is a mixture of a plurality of fluorine-containing ether compounds having different chain lengths of the polyfluoropolyether chain, the "molecular weight" of the polyfluoropolyether chain is a number average molecular weight calculated by determining the number (average value) of oxyfluoroalkylene units based on the terminal groups, by $^1$H-NMR and $^{19}$F-NMR. The terminal groups are, for example, $R^f$ in formula (A1) or T in formula (A1) or formula (A2).

If the fluorine-containing ether compound is a fluorine-containing ether compound having a single polyfluoropolyether chain length, the "molecular weight" of the polyfluoropolyether chain is the molecular weight calculated by determining the structure of $R^f$ by $^1$H-NMR and $^{19}$F-NMR.

The word "to" when used to indicate a numerical range means that the numerical value described before and the numerical value described after that are included as the lower limit value and the upper limit value.

[Fluorine-Containing Ether Compound]

The fluorine-containing ether compound of the present invention (hereinafter, referred to as "the present compound") is a fluorine-containing ether compound represented by the following formula (A1) or formula (A2):

Formula (A1)

$$R^f—O—(R^{f1}O)_m—R^{f2}[—R^1—C(—R^2—T)_a(—R^3)_{3-a}]_b$$

Formula (A2)

$$[(T\text{-}R^2—)_a(R^3—)_{3-a}C—R^1—]_bR^{f2}—O—(R^{f1}O)_m—R^{f2}[—R^1—C(—R^2—T)_a(—R^3)_{3-a}]_b$$

wherein $R^f$ is a fluoroalkyl group having 1 to 20 carbon atoms, $R^{f1}$ is a fluoroalkylene group having 1 to 6 carbon atoms, $R^{f2}$ is an organic group having a valence of (1+b), where at least a carbon atom bonded to $R^1$ bonds to a fluorine atom, and when there is a plurality of $R^{f2}$, the $R^{f2}$ may be the same or different, $R^1$ is an alkylene group having 1 to 20 carbon atoms, and when there is a plurality of the $R^1$ may be the same or different, $R^2$ is an alkylene group having 2 to 10 carbon atoms and optionally a fluorine atom, and a plurality of $R^2$ may be the same or different, $R^3$ is a hydrogen atom or an alkyl group having 1 to 10 carbon atoms and optionally a fluorine atom, and when there is a plurality of $R^3$, the plurality of $R^3$ may be the same or different, T is $—Si(R)_{3-c}(L)_c$, and a plurality of T may be the same or different, R is an alkyl group, L is a hydrolytic group or a hydroxyl group, and 2 or more L in T may be the same or different, m is an integer from 1 to 20, a is an integer from 1 to 3, and when there is a plurality of a, the plurality of a may be the same or different, b is an integer of 1 or more, and when there is a plurality of b, the plurality of b may be the same or different, c is 2 or 3, and a plurality of c may be the same or different, and when b is 1, a is 2 or 3.

The present compound has a polyfluoropolyether chain $[R^f—O—(R^{f1}O)_m—]$ or $[—O—(R^{f1}O)_m—]$, a reactive silyl group, and a specific connecting group $—R^{f2}[—R^1—C(—R^2—)_a]_b$ that connects the polyfluoropolyether chain and the reactive silyl group.

Compound (A1) is a compound having a structure of a "monovalent polyfluoropolyether chain-connecting group-reactive silyl group," and compound (A2) is a compound having a structure of a "reactive silyl group-connecting group-divalent polyfluoropolyether chain-connecting group-reactive silyl group."

The present compound has a polyfluoropolyether chain. The present compound having a polyfluoropolyether chain has excellent fingerprint stain removability of the surface layer. At least at one terminal, the present compound also has a reactive silyl group. The present compound having a reactive silyl group at a terminal forms a strong chemical bond with the substrate, and so has excellent abrasion resistance of the surface layer. Further, the present compound is composed of a carbon chain in which the connecting group does not contain an ether bond (—C—O—C—). Therefore, chemical stability is better compared with the connecting groups including an ether bond that are conventionally widely used. As a result, a surface layer formed from the present compound exhibits excellent durability, such as abrasion resistance, chemical resistance, and light resistance. Since the present compound can form a surface layer that exhibits high lubricity, water and oil repellency, and the like on the surface of the substrate, the present compound can be suitably used for a surface treatment agent.

$R^f$ is a fluoroalkyl group having 1 to 20 carbon atoms, and as a result the abrasion resistance and the fingerprint stain removability of the surface layer are even better. From the perspective of having even better abrasion resistance and fingerprint stain removability of the surface layer, the $R^f$ fluoroalkyl group preferably has 1 to 6 carbon atoms, more preferably 1 to 4 carbon atoms, and particularly preferably 1 to 3 carbon atoms.

From the perspective of having even better abrasion resistance and fingerprint stain removability of the surface layer, the $R^f$ fluoroalkyl group is preferably a perfluoroalkyl group. A compound in which $R^f$ is a perfluoroalkyl group has a $CF_3$— at a terminal. When the compound has a $CF_3$— at a terminal, a surface layer having a low surface energy can be formed, so that the abrasion resistance and fingerprint stain removability of the surface layer are even better.

Examples of the $R^f$ fluoroalkyl group include $CF_3$—, $CF_3CF_2$—, $CF_3CF_2CF_2$—, $CF_3CF_2CF_2CF_2$—, $CF_3CF_2CF_2CF_2CF_2$—, $CF_3CF_2CF_2CF_2CF_2CF_2$—, $CF_3CF(CF_3)$—, and the like.

$(R^{f1}O)_m$ preferably has a structure represented by the following formula ($R^{f1}$-1), from the perspective of having even better abrasion resistance and fingerprint stain removability of the surface layer.

Formula ($R^{f1}$-1)

$$(R^{f11}O)_{m1}(R^{f12}O)_{m2}(R^{f13}O)_{m3}(R^{f14}O)_{m4}(R^{f15}O)_{m5}(R^{f16}O)_{m6}$$

wherein, $R^{f11}$ is a fluoroalkylene group having 1 carbon atom, $R^{f12}$ is a fluoroalkylene group having 2 carbon atoms, $R^{f13}$ is a fluoroalkylene group having 3 carbon atoms, $R^{f14}$ is a fluoroalkylene group having 4 carbon atoms, $R^{f15}$ is a fluoroalkylene group having 5 carbon atoms, $R^{f16}$ is a fluoroalkylene group having 6 carbon atoms, and m1, m2, m3, m4, m5, and m6 each independently represent an integer of 0 or 1 or more, m1+m2+m3+m4+m5+m6 is an integer of 1 to 200, and when there is a plurality of $R^{f11}$ to $R^{f16}$, the plurality of $R^{f11}$ to $R^{f16}$ may be the same or different.

It is noted that the binding order of $(R^{f11}O)$ to $(R^{f16}O)$ in formula ($R^{f1}$-1) is arbitrary. The m1 to m6 of formula ($R^{f1}$-1) represent the number of $(R^{f11}O)$ to $(R^{f16}O)$, respectively, and do not represent these arrangements. For example, $(R^{f15}O)_{m5}$ represents that the number of $(R^{f15}O)$ is m5, and does not represent the block arrangement structure of $(R^{f15}O)_{m5}$. Similarly, the order in which $(R^{f11}O)$ to $(R^{f16}O)$ are written does not represent the binding order of each unit.

Further, the fluoroalkylene group having 3 to 6 carbon atoms may be a straight chain fluoroalkylene group or a fluoroalkylene group having a branched or ring structure.

Specific examples of $R^{f11}$ include CHF and $CF_2$. Specific examples of $R^{f12}$ include $CF_2CF_2$, $CF_2CHF$, $CF_2CH_2$, and the like. Specific examples of $R^{f13}$ include $CF_2CF_2CF_2$, $CF_2CF_2CHF$, $CF_2CHFCF_2$, $CF_2CF_2CH_2$, $CF_2CH_2CF_2$, $CF(CF_3)CF_2$, and the like. Specific examples of $R^{f14}$ include $CF_2CF_2CF_2CF_2$, $CF_2CF_2CF_2CH_2$, $CHFCF_2CF_2CF_2$, $CF_2CH_2CF_2CF_2$, $CF(CF_3)CF_2CF_2$, a perfluorocyclobutane-1,2-diyl group, and the like. Specific examples of $R^{f15}$ include $CF_2CF_2CF_2CF_2CF_2$, $CF_2CF_2CF_2CF_2CH_2$, $CHFCF_2CF_2CF_2CF_2$, $CF_2CF_2CH_2CF_2CF_2$, and the like. Specific examples of $R^{f16}$ include $CF_2CF_2CF_2CF_2CF_2CF_2$, $CF_2CF_2CF_2CF_2CF_2CH_2$, $CF_2CF_2CF_2CF_2CF_2CHF$, and the like.

$R^{f2}$ is an organic group having a valence of (1+b), where at least a carbon atom bonded to $R^1$ bonds to a fluorine atom. That is, $R^{f2}$ is an organic group having b number of partial structures "-CQF-*" (in which Q is a hydrogen atom or a fluorine atom, and —* is a bond binding to $R^1$). $R^{f2}$ preferably has 1 to 6 carbon atoms. Examples of the organic group include a hydrocarbon group optionally having a substituent. Examples of the hydrocarbon group include a straight chain or branched alkyl group, a cycloalkyl group, an aryl group, and combinations thereof. The hydrocarbon group may have a double bond or triple bond in the carbon chain. Examples of the combinations include combinations of an alkyl group and an aryl group, combinations of a alkyl group and a cycloalkyl group, and the like.

The substituent that the hydrocarbon group may optionally have is preferably a halogen atom, among which a fluorine atom is more preferred. From perspectives such as ease of production, b is preferably 1 to 10, and more preferably is 1 to 6.

In the case where b is 1, $R^{f2}$ is a divalent group. Examples of $R^{f2}$ in this case include fluoroalkylene groups optionally having a substituent and optionally having a hetero atom or a bond other than a (fluoro)alkylene group in the carbon chain. From the perspective of the durability of the present compound, $R^{f2}$ when b is 1 is preferably a fluoroalkylene group having 1 to 6 carbon atoms. Specific examples of $R^{f2}$ in this case include —CHF—*, —$CF_2$—*, $CF_2CF_2$—*, $CF_2CHF$—*, $CH_2CF_2$—*, $CF_2CF_2CF_2$—*, $CF_2CF_2CHF$—*, $CF_2CHFCF_2$—*, $CH_2CF_2CF_2$—*, $CF_2CH_2CF_2$—*, $CF(CF_3)CF_2$—*, $CF_2CF_2CF_2CF_2$—*, $CH_2CF_2CF_2CF_2$—*, $CHFCF_2CF_2CF_2$—*, $CF_2CH_2CF_2CF_2$—*, $CF(CF_3)CF_2CF_2$—*, $CF_2CF_2CF_2CF_2CF_2$—*, $CH_2CF_2CF_2CF_2CF_2$—*, $CHFCF_2CF_2CF_2CF_2$—*, $CF_2CF_2CH_2CF_2CF_2$—*, $CF_2CF_2CF_2CF_2CF_2CF_2$—*, $CH_2CF_2CF_2CF_2CF_2CF_2$—*, $CF_2CF_2CF_2CF_2CF_2CHF$—*, and the like.

In the case where b is 2 or more, $R^{f2}$ is a group with a valence of (1+b) having one or more branch points P selected from a tertiary carbon atom, a quaternary carbon atom, and a ring structure.

From the perspective of ease of production of the present compound and the perspective of durability, such as the abrasion resistance, chemical resistance, and light resistance of the surface layer, the carbon atoms constituting the branch points are preferably a tertiary carbon atom or a quaternary carbon atom.

Examples of the ring structure constituting a branch point include, from the perspective of ease of production of the present compound and the perspective of durability, such as the abrasion resistance, chemical resistance, and light resistance of the surface layer, a 3- to 8-member alicyclic ring, a 6- to 8-member ring aromatic ring, a 3- to 8-member heterocyclic ring, a condensed ring consisting of two or more of these rings, and the like. From the perspective of durability, such as the abrasion resistance, chemical resistance, and light resistance of the surface layer, a ring structure selected from a 3- to 8-member alicyclic ring, a 6- to 8-member ring aromatic ring, and a condensed ring of these is preferred. Examples of the ring structure constituting the branch points include the ring structure shown in the following formula. The following ring structure may be substituted with a fluorine atom. The ring structure may have an alkyl group, a cycloalkyl group, an alkenyl group, an allyl group, or the like optionally having a halogen atom as a substituent

[Formula 1]

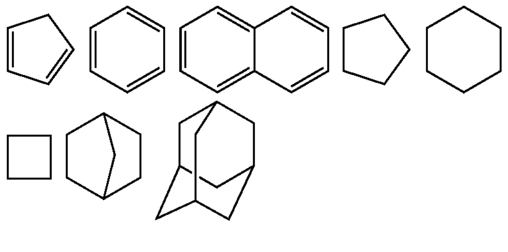

As $R^{f2}$, a combination of two or more divalent fluoroalkylene groups and one or more branch points P is preferred.

Preferred specific examples when $R^{f2}$ has a valance of 3 or more are shown below. In the following formulas, $R^F$ represents $(R^{f1}O)_m$, and $R^F$ and $R^1$ do not constitute $R^{f2}$.

[Formula 2]

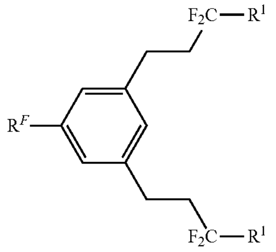

-continued

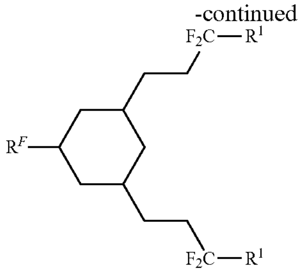

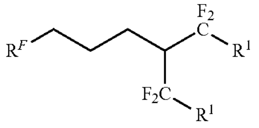

$R^1$ is an alkylene group having 1 to 20 carbon atoms. $R^1$ does not have a fluorine atom. Since $R^1$ is an alkylene group that does not contain an ether bond, the durability and fingerprint stain removability of the surface layer are even better. $R^1$ preferably has 5 to 20 carbon atoms, and more preferably 7 to 10 carbon atoms, because the durability and fingerprint stain removability of the surface layer are even better. Further, from the perspective of the wear resistance of the surface layer, $R^1$ preferably has an odd number of carbon atoms, and more preferably 3, 5, 7 or 9.

$R^2$ is an alkylene group having 2 to 10 carbon atoms and optionally a fluorine atom. Since $R^2$ is an alkylene group that does not contain an ether bond, the durability and fingerprint stain removability of the surface layer are even better. From the perspective of having even better durability and fingerprint stain removability of the surface layer, $R^2$ preferably has 3 to 10 carbon atoms. From the perspective of having even better durability and fingerprint stain removability of the surface layer, of a plurality of $R^2$, at least one of $R^2$ preferably has 3 or more carbon atoms, and all of the plurality of $R^2$ preferably have 3 or more carbon atoms. Further, from the perspective of the durability and the like of the surface layer, an alkylene group in which $R^2$ does not have a fluorine atom is preferred.

In the present compound, the number of "$—CH_2—$" in the molecule, that is, the number of carbon atoms not bonded to the fluorine atom, is preferably 8 to 30, and preferably 10 to 20. In particular, the total number of $—CH_2—$ included in $R^1$ and $R^2$ is preferably 8 to 30, and preferably 10 to 20. Such a present compound has even better durability and fingerprint stain removability of the surface layer.

$R^3$ is a hydrogen atom or an alkyl group having 1 to 10 carbon atoms and optionally a fluorine atom. Since $R^3$ is a hydrogen atom or an alkyl group optionally having a fluorine atom, the durability and fingerprint stain removability of the surface layer are even better. From the perspective of having even better durability and fingerprint stain removability of the surface layer, $R^3$ is preferably a hydrogen atom or an alkyl group having 1 to 8 carbon atoms and optionally a fluorine atom, and more preferably is a hydrogen atom.

T is $—Si(R)_{3-c}(L)_c$, and is a reactive silyl group.

The reactive silyl group is a group in which one or both of a hydrolytic group and a hydroxyl group are bonded to a silicon atom.

The hydrolyzable group is a group that turns into a hydroxyl group by a hydrolysis reaction. That is, the hydrolyzable silyl group turns into a silanol group (Si—OH) by a hydrolysis reaction. The silanol groups further undergo a dehydration condensation reaction between molecules to form Si—O—Si bonds. In addition, the silanol groups undergo a dehydration condensation reaction with hydroxyl groups on the surface of substrate (substrate-OH) to form a chemical bond (substrate-O—Si).

Examples of the hydrolyzable group include an alkoxy group, an aryloxy group, a halogen atom, an acyl group, an acyloxy group, and an isocyanate group. The alkoxy group is preferably an alkoxy group having 1 to 6 carbon atoms. The halogen atom is preferably a chlorine atom. The acyl group is preferably an acyl group having 1 to 6 carbon atoms. The acyloxy group is preferably an acyloxy group having 1 to 6 carbon atoms.

From the perspective of ease of production of the present compound, the hydrolyzable group is preferably an alkoxy group or a halogen atom. From the perspective that the amount of outgas at the time of application is small and the storage stability of the present compound is excellent, the hydrolyzable group is preferably an alkoxy group having 1 to 4 carbon atoms. When long-term storage stability of the present compound is required, an ethoxy group is particularly preferred, and when the reaction time after coating is to be set to a short time, a methoxy group is particularly preferred.

From the perspective of ease of production of the present compound, the number of carbon atoms of the alkyl group of R is preferably 1 to 6, more preferably 1 to 3, and particularly preferably 1 to 2.

From the perspective of stronger adhesion between the surface layer and the substrate, c is preferably 2 or 3, and more preferably is 3.

A plurality of T may be the same or different. From the perspective of ease of production of the present compound, T are preferably the same group.

Further, from the perspective of the durability of the surface layer, it is preferred that two or more T are arranged at each terminal, and from such a viewpoint, when b is 1, a is 2 or 3.

Examples of the present compound include the compounds of the following formulas. The compounds of the following formulas are industrially easy to produce, easy to handle, and have even better water and oil repellency, abrasion resistance, fingerprint stain removability, lubricity, chemical resistance, light resistance and chemical resistance of the surface layer. Further, from the perspective of durability, it is preferred that the present compound has a weight average molecular weight (Mw)/number average molecular weight (Mn) of 1.2 or less.

[Formula 3]
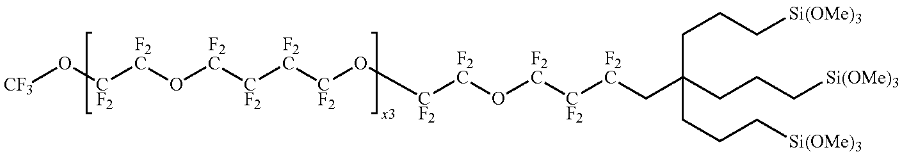
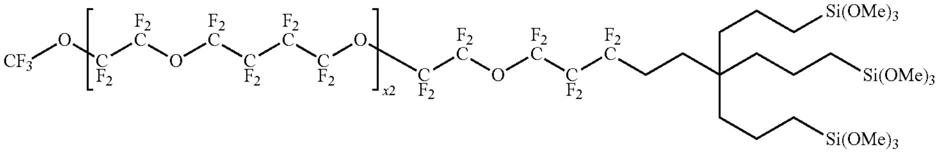
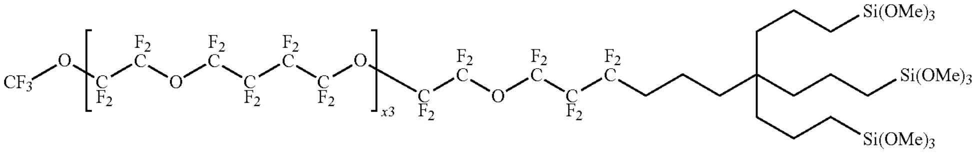
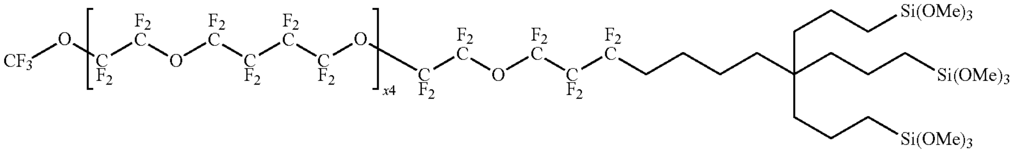
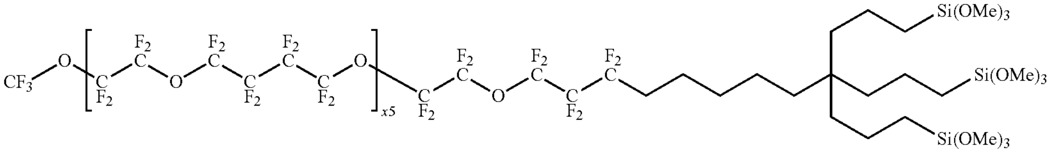
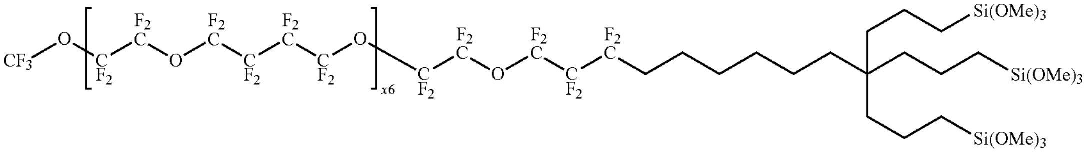
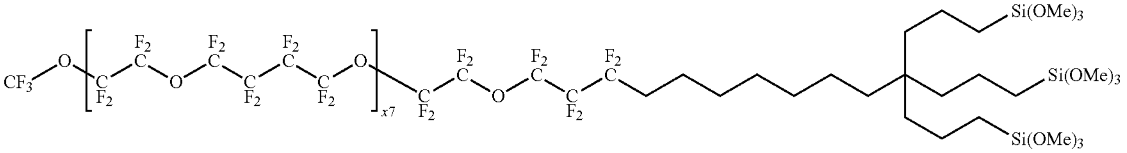
[Formula 4]
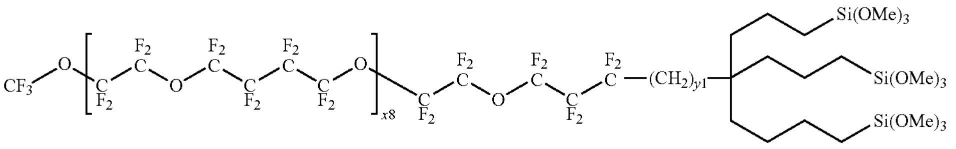
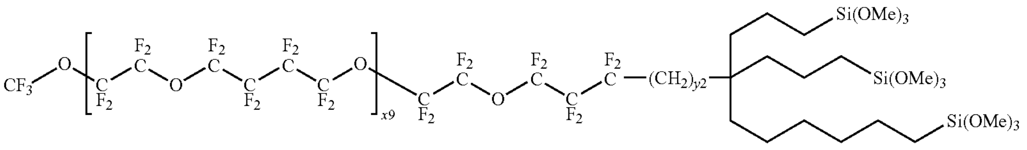
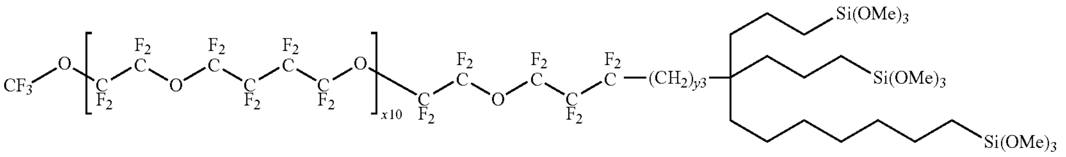

-continued

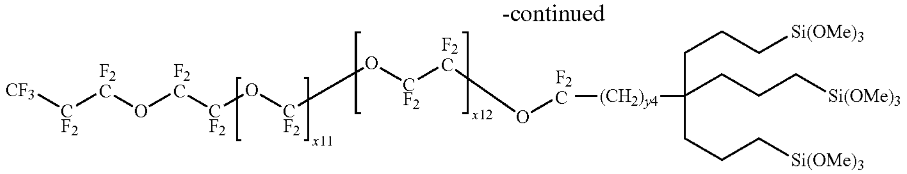

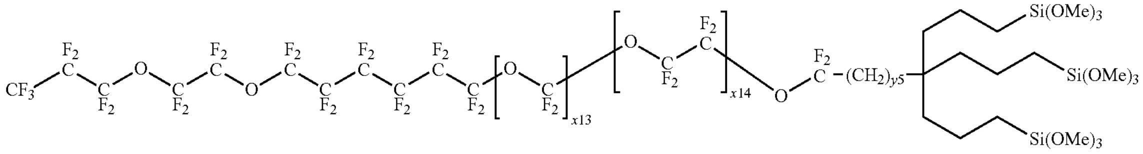

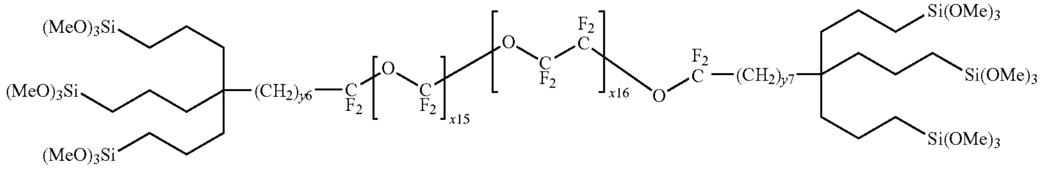

It is noted that x1 to x16 in the formulas are each independently an integer of 1 to 100, and yl to y7 are each independently an integer of 1 to 7. (Method for producing compound (A1) and compound (A2))

Compound (A1) can be produced, for example, by conducting hydrosilylation between the following compound (A11) and compound (1a). Compound (A2) can be produced, for example, by conducting hydrosilylation between the following compound (A21) and compound (1a).

In the formulas, $L^2$ is a sulfonate group, $R^{21}$ is a single bond or an alkylene group having 1 to 19 carbon atoms, X is a chlorine atom, a bromine atom, or an iodine atom, and the other reference signs are the same as those in formula (A11) or formula (A21).

Formula (A11)

$$R^f—O—(R^{f1}O)_m—R^{f2}[—R^1—C(—R^{20}—CH=CH_2)_a(—R^3)_{3-a}]_b$$

Formula (A21)

$$[(CH_2=CH—R^{20}—)_a(R^3—)_{3-a}C—R^1—]_bR^{f2}—O—(R^{f1}O)_m—R^{f2}[—R^1—C(—R^{20}—CH=CH_2)_a(—R^3)_{3-a}]_b$$

Formula (1a)

$$HSi(R)_{3-c}(L)_c$$

In the formulas, $R^{20}$ is a single bond or an alkylene group having 1 to 8 carbon atoms and optionally a fluorine atom, and the reference signs other than $R^{20}$ are the same as the reference signs in formula (A1) or formula (A2).

$—R^{20}—CH=CH_2$ becomes $R^2$ after the hydrosilylation. Examples of $R^{20}$ include the same groups as those of $R^2$, and the preferred forms are also the same.

(Method for Producing Compound (all) and Compound (A21))

Compound (A11) can be produced, for example, by reacting the following compound (A12) with the following compound (B2). Compound (A21) can be produced, for example, by reacting the following compound (A22) with the following compound (B2).

Formula (A12)

$$R^f—O—(R^{f1}O)_m—R^{f2}—CH_2—L^2$$

Formula (A22)

$$L^2—CH_2—R^{f2}—O—(R^{f1}O)_m—R^{f2}—CH_2—L^2$$

Formula (B2)

$$(CH_2=CH—R^{20}—)_a(R^3—)_{3-a}C—R^{21}—MgX$$

The sulfonate group of compound (A12) or compound (A22) and MgX of compound (B2) react as shown in the following scheme (1) (Grignard reaction). Scheme (1)

$$—R^{f2}—CH_2—L^2 + XMg—R^{21}— \longrightarrow —R^{f2}—CH_2—R^{21}$$

In the formula, each reference sign in scheme (1) is as described above.

It is noted that $CH_2—R^{21}$ after the reaction corresponds to $R^1$ of the present compound.

$L^2$ is a sulfonate group ($—O—SO_2—R^{22}$), which leaves by a reaction with a Grignard reagent. $R^{22}$ is an organic group. By selecting a sulfonate group as $L^2$, the reaction of scheme (1) can be carried out under relatively mild conditions and enables to achieve a high yield.

Specific examples of the sulfonate group include a tosylate group (OTs), a mesylate group (OMs), a triflate group (OTf), a nonaflate group (ONf), and the like. Among these, from the perspective of the reaction yield of scheme (1), a triflate group is preferred.

Compound (A12) or compound (A22) can be produced by sulfonation in which trifluoromethane sulfonic anhydride, tosyl chloride, mesyl chloride, or the like are reacted with a compound represented by the following compound (A13) or compound (A23) in the presence of an organic amine compound such as triethylamine or pyridine.

Formula (A13)

$$R^f—O—(R^{f1}O)_m—R^{f2}—CH_2—OH$$

Formula (A23)

$$L^2—CH_2—R^{f2}—O—(R^{f1}O)_m—R^{f2}—CH_2—OH$$

Compound (A13) and compound (A23) can be produced by referring to, for example, International Patent Publication No. WO 2017/038830 and the like.

Compound (B2) can be produced, for example, by reacting the following compound (B1) with magnesium metal.

Formula (B1)

$$(CH_2{=}CH—R^{20}—)_a(R^3—)_{3-a}C—R^{21}—X$$

In the formula, $R^{20}$, $R^{21}$, $R^3$, X, and a are the same as for compound (B2).

Compound (B1) is obtained, for example, by halogenating a hydroxy group of an unsaturated alcohol. The unsaturated alcohol may be synthesized or a commercially available product may be used.

Suitable specific examples of compound (B2) include the following.

[Formula 5]

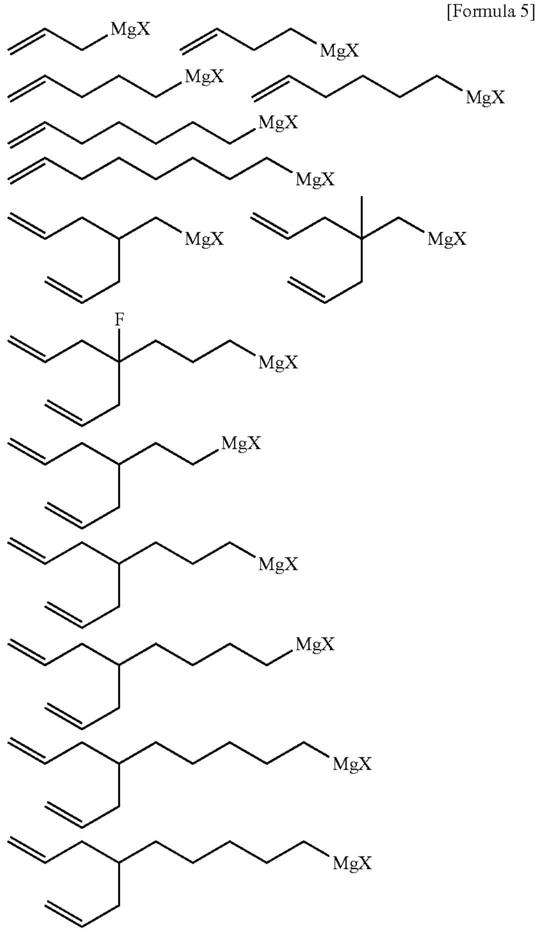

-continued

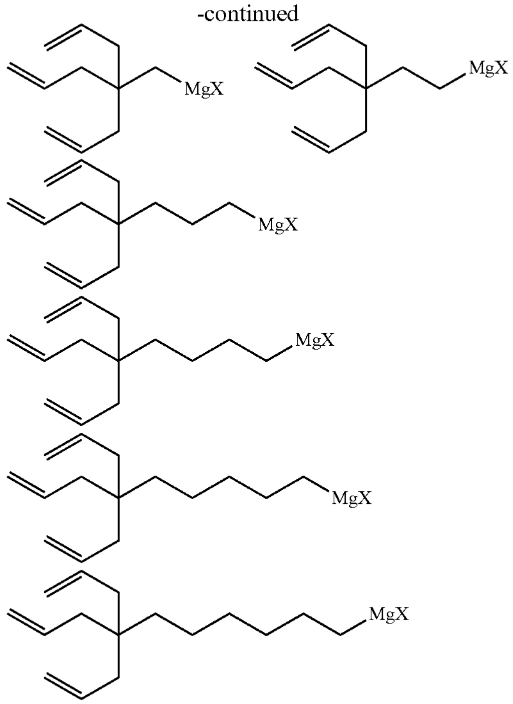

In the reaction of scheme (1), from the viewpoint of improving the yield of the target product, the amount of compound (B2) that is used is preferably from 1 to 30 equivalents based on the total number of sulfonate groups $L^2$ of compound (A12) or compound (A22), more preferably from 3 to 20 equivalents, and further preferably from 5 to 15 equivalents.

In the reaction of scheme (1), from the perspectives of improving reactivity and enabling a high yield to be achieved, it is preferred to use a transition metal compound as a catalyst. The transition metal compound can be appropriately selected from known catalysts used in Grignard reactions. The transition metal compound is preferably a compound including an element in Groups 3 to 12 of the periodic table as the transition metal, and among those a compound including an element in Groups 8 to 11 is preferred. Among the Group 8 to 11 elements, it is preferred to include one or more elements selected from copper, nickel, palladium, cobalt, and iron, and more preferred to include copper.

When the transition metal compound includes copper, the valency of the copper may be a 0, 1, 2, or 3, but from the perspective of catalytic ability, a salt or a complex salt of copper having a valency of 1 or 2 is preferred. Further, from the perspective of availability and the like, copper chloride is more preferred.

The amount of the transition metal compound that is used is, for example, based on the total number of sulfonate groups $L^2$, 0.1 to 50 mol %, preferably 1 to 30 mol %, and more preferably 2 to 20 mol %.

Further, a transition metal compound incorporated with a ligand may also be used. Applying a ligand improves the yield of the target product. However, in the present production method, a ligand is not necessary to be applied since a sufficient yield can be achieved even if a ligand is not applied.

Examples of the ligand include 1,3-butadiene, phenylpropyne, tetramethylethylenediamine (TMEDA), and the like.

When applying a ligand, from the perspective improving the yield of the target product, it is preferred to use 0.01 to 2.0 equivalents based on the total number of sulfonate groups $L^2$, and more preferred to use 0.1 to 1.2 equivalents.

The reaction of scheme (1) is usually conducted in a solvent. The solvent can be appropriately selected from the solvents that can dissolve compound (A12), compound (A13), and compound (B2). The solvent may be a single kind of solvent or may be a mixed solvent in which two or more kinds of solvents are combined.

For example, when compound (A12) or compound (A13) is a compound having a relatively low fluorine atom content (the ratio of fluorine atoms with respect to the molecular weight of compound molecule), the solvent is not particularly limited as long as it is a solvent that is inert to the reaction. Among solvents inert to the reaction, an ether-based solvent such as diethyl ether, tetrahydrofuran, and dioxane is preferred, and tetrahydrofuran is more preferred.

Further, when compound (A12) or compound (A13) is a compound having a relatively high fluorine atom content, a mixed solvent obtained by combining the ether-based solvent and a fluorine-based solvent is preferred.

Examples of the fluorine-based solvent include hydrofluorocarbons (1H,4H-perfluorobutane, 1H-perfluorohexane, 1H-tridecafluorohexane (AC-2000), 1,1,1,3,3-pentafluorobutane, 1,1,2,2,3,3,4-heptafluorocyclopentan, 2H,3H-perfluoropentan, and the like), hydrochlorofluorocarbons (3,3-dichloro-1,1,1,2,2-pentafluoropropane, 1,3-dichloro-1,1,2,2,3-pentafluoropropane (HCFC-225cb), and the like), hydrofluoroethers ($CF_3CH_2OCF_2CF_2H$ (AE-3000), 1,1,1,2,2,3,3,4,4,5,5,6,6-tridecafluorooctane (AC-6000), (perfluorobotoxy)methane, (perfluorobutoxy)ethane, and the like), hydrochlorofluoroolefins ((Z)-1-chloro-2,3,3,4,4,5,5-heptafluoro-1-pentene (HCFO-1437dycc (Z) form), (E)-1-chloro-2,3,3,4,4,5,5-heptafluoro-1-pentene (HCFO-1437dycc (E) form, (Z)-1-chloro-2,3,3-trifluoro-1-propene (HCFO-1233yd (Z) form), (E)-1-chloro-2,3,3-trifluoro-1-propene (HCFO-1233yd (E) form), and the like), fluorine-containing aromatic compounds (perfluorobenzene, m-bis (trifluoromethyl)benzene (SR-sorbent), p-bis (trifluoromethyl) benzene, and the like), and the like.

The reaction of scheme (1) can be carried out, for example, by preparing a solution including compound (A12) or compound (A13), adding a transition metal compound and a ligand as necessary, and then adding a separately prepared compound (B2) solution.

The reaction temperature of scheme (1) may be, for example, −20° C. to 66° C. (boiling point of tetrahydrofuran), and −20° C. to 40° C. is preferred.

The fluorine-containing-compound-containing composition of the present invention (hereinafter, referred to as "the present composition") may contain compound (A1) and compound (A2), and may contain one or more selected from compound (A1) and compound (A2), and an additional fluorine-containing ether compound. The present composition does not include the liquid medium described later.

Examples of the additional fluorine-containing ether compound include fluorine-containing ether compounds that are produced as by-products in the production process of the present compound (hereinafter, referred to as "by-product fluorine-containing ether compounds"), known fluorine-containing ether compounds used in similar applications as the present compound, and fluorine-containing oils. As the additional fluorine-containing ether compound, a compound that is less likely to cause a deterioration in the properties of the present compound is preferred.

Examples of fluorine-containing oils include polytetrafluoroethylene (PTFE), ethylene-chlorotrifluoroethylene copolymer (ECTFE), polyvinylidene fluoride (PVDF), polyvinyl fluoride (PVF), polychlorotrifluoroethylene (PCTFE), and the like.

Examples of by-product fluorine-containing ether compounds include unreacted fluorine-containing ether compounds at the time of synthesis of the present compound. If the present composition includes by-product-containing fluorine compounds, a purification step for removing the by-product-containing fluorine compounds or reducing the amount of such by-product-containing fluorine compounds may be skipped.

Examples of known fluorine-containing ether compounds include those described in the following literature:

The perfluoropolyether-modified aminosilanes described in Japanese Unexamined Patent Application Publication No. H11-029585, the silicon-containing organic fluorine-containing polymers described in Japanese Patent No. 2874715, the organic silicon compounds described in Japanese Unexamined Patent Application Publication No. 2000-144097, the perfluoropolyether-modified aminosilanes described in Japanese Unexamined Patent Application Publication No. 2000-327772, the fluorinated siloxanes described in Published Japanese Translation of PCT International Publication for Patent Application, No. 2002-506887, the organic silicone compounds described in Published Japanese Translation of PCT International Publication for Patent Application, No. 2008-534696, the fluorinated modified hydrogen-containing polymers described in Japanese Patent No. 4138936, the compounds described in United States Patent Publication No. 2010/0129672, International Patent Publication No. WO 2014/126064, and Japanese Unexamined Patent Application Publication No. 2014-070163, the organosilicon compounds described in International Patent Publication No. WO 2011/060047 and International Patent Publication No. WO 2011/059430, the fluorine-containing organosillane compounds described in International Patent Publication No. WO 2012/064649, the fluorooxyalkylene group-containing polymers described in Japanese Unexamined Patent Application Publication No. 2012-72272, the fluorine-containing ether compounds described in International Patent Publication No. WO 2013/042732, International Patent Publication No. WO 2013/121984, International Patent Publication No. WO 2013/121985, International Patent Publication No. WO 2013/121986, International Patent Publication No. WO 2014/163004, Japanese Unexamined Patent Application Publication No. 2014-080473, International Patent Publication No. WO 2015/087902, International Patent Publication No. WO 2017/038830, International Patent Publication No. WO 2017/038832, and International Patent Publication No. WO 2017/187775, the perfluoro(poly)ether-containing silane compounds described in Japanese Unexamined Patent Application Publication No. 2014-218639, International Patent Publication No. WO 2017/022437, International Patent Publication No. WO 2018/079743, and International Patent Publication No. WO 2018/143433, the fluoropolyether group-containing-polymer-modified silanes described in Japanese Unexamined Patent Application Publication No. 2015-199906, Japanese Unexamined Patent Application Publication No. 2016-204656, Japanese Unexamined Patent Application Publication No. 2016-210854, and Japanese Unexamined Patent Application Publication No. 2016-222859, and the fluorine-containing ether compounds described in International Patent Publication No. WO 2018/216630, International Patent Publication No. WO 2019/039226, International Patent Publication No. WO 2019/039341, International Patent Publication No. WO 2019/039186, International Patent Publication No. WO 2019/044479, Japanese Unexamined Patent Application Publication No. 2019-44158, and International Patent Publication No. WO 2019/163282.

Further, examples of commercially available fluorine-containing ether compounds include the KY-100 series (KY-178, KY-185, KY-195, and the like) manufactured by Shin-Etsu Chemical Co., Ltd., Afluid (register trade mark) 5550 manufactured by AGC Inc., Optool (register trade mark) DSX, Optool (register trade mark) AES, Optool (register trade mark) UF503, Optool (register trade mark) UD509 manufactured by Daikin Industries, Ltd., and the like.

The proportion of the present compound in the present composition is less than 100% by mass, preferably 60% by mass or more, more preferably 70% by mass or more, and further preferably 80% by mass or more.

If the present composition includes an additional fluorine-containing ether compound, the proportion of the additional fluorine-containing ether compound based on the present compound and the additional fluorine-containing ether compound in total in the present composition is preferably 40% by mass or less, more preferably 30% by mass or less, and further preferably 20% by mass or less.

The proportion of the present compound and the additional fluorine-containing ether compound in total in the present composition is preferably 80% by mass or more, and more preferably 85% by mass or more.

If the content of the present compound and the additional fluorine compound is within the above range, the surface layer has excellent water and oil repellency, abrasion resistance, fingerprint stain removability, lubricity, and appearance.

[Coating Liquid]

The coating liquid of the present invention (hereinafter, also referred to as the "present coating liquid") includes the present compound or the present composition and a liquid medium. The coating liquid may be a liquid, a solution, or a dispersion.

The present coating liquid contains at least the present compound or the present composition, and may contain impurities such as by-products produced in the production process of the present compound.

The concentration of the present compound or the present composition is preferably 0.001 to 40% by mass of the coating liquid, preferably 0.01 to 20% by mass, and more preferably 0.1 to 10% by mass.

The liquid medium is preferably an organic solvent. The organic solvent may be a fluorine-based organic solvent, may be a non-fluorine-based organic solvent, or may include both solvents.

Examples of the fluorine-based organic solvent include fluorinated alkanes, fluorinated aromatic compounds, fluoroalkyl ethers, fluorinated alkylamines, fluoroalcohols, and the like.

As the fluorinated alkane, a compound having 4 to 8 carbon atoms is preferred. Examples of commercially available products include $C_6F_{13}H$ (manufactured by AGC Inc., Asahiklin (register trade mark) AC-2000), $C_6F_{13}C_2H_5$ (manufactured by AGC, Asahiklin (register trade mark) AC-6000), $C_2F_5CHFCHFCF_3$ (Manufactured by Chemours, Vertrel (register trade mark) XF), and the like.

Examples of the fluorinated aromatic compound include hexafluorobenzene, trifluoromethylbenzene, perfluorotoluene, bis(trifluoromethyl)benzene, and the like.

As the fluoroalkyl ether, a compound having 4 to 12 carbon atoms is preferred. Examples of commercially available products include $CF_3CH_2OCF_2CF_2H$ (manufactured by AGC Inc., Asahiklin (register trade mark) AE-3000), $C_4F_9OCH_3$ (manufactured by 3M, Novec (register trade mark) 7100), $C_4F_9OC_2H_5$ (manufactured by 3M, Novec (register trade mark) 7200), $C_2F_5CF(OCH_3)C_3F_7$ (manufactured by 3M, Novec (register trade mark) 7300), and the like.

Examples of the fluorinated alkylamine include perfluorotripropylamine, perfluorotributylamine, and the like.

Examples of the fluoroalcohol include 2,2,3,3-tetrafluoropropanol, 2,2,2-trifluoroethanol, hexafluoroisopropanol, and the like.

As the non-fluorine-based organic solvent, compounds consisting only of hydrogen atoms and carbon atoms and compounds consisting only of hydrogen atoms, carbon atoms, and oxygen atoms are preferred. Examples thereof include hydrocarbon-based organic solvents, alcohol-based organic solvents, ketone-based organic solvents, ether-based organic solvents, and ester-based organic solvents.

The present coating liquid preferably includes 75 to 99.999% by mass, preferably 85 to 99.99% by mass, and particularly preferably 90 to 99.9% by mass % of the liquid medium.

The present coating liquid may include other components in addition to the present compound or the present composition and the liquid medium, to the extent that the effects of the present invention are not impaired.

Examples of the other components include known additives such as acid catalysts and basic catalysts that promote the hydrolysis and condensation reactions of the hydrolytic silyl group.

The content of other components in the present coating liquid is preferably 10% by mass or less, and 1% by mass or less is more preferred.

The concentration of the present compound and other components in total in the present coating liquid or the concentration of the present composition and other components in total (hereinafter, also referred to as the "solid content") is preferably 0.001 to 40% by mass, preferably 0.01 to 20% by mass, more preferably 0.01 to 10% by mass, and more preferably 0.01 to 1% by mass. The solid content concentration of the coating liquid is a value calculated from the mass of coating liquid before heating and the mass after heating at 120° C. for 4 hours in a convection dryer.

[Article]

The article of the present invention (hereinafter, also referred to the "present article") has a surface layer formed from the present compound or the present composition on a surface of a substrate. The surface layer may be formed on a part of the surface of the substrate or on all of the surface of the substrate. The surface layer may be extended in a film shape on the surface of the substrate, or may be present in the form of a dot-shaped.

The surface layer includes the present compound in a state in which a part or all of the hydrolyzable silyl groups of the present compound have been hydrolyzed and the silanol groups have undergone dehydration condensation.

The thickness of the surface layer is preferably 1 to 100 nm, and particularly preferably 1 to 50 nm. When the thickness of the surface layer is 1 nm or more, the effect of the surface treatment tends to be sufficiently obtained. When the thickness of the surface layer is 100 nm or less, utilization efficiency is high. The thickness of the surface layer can be calculated from the oscillation period of an interference pattern of reflected X-rays obtained by an X-ray reflectance method using an X-ray diffractometer for thin film analysis (manufactured by Rigaku Corporation, ATX-G).

The substrate may be a substrate requiring water and oil repellency to be imparted. Examples thereof include substrates that may be used by contacting another object (e.g., a stylus) or a human finger, substrates that may be held by the fingers of a person during operation, and substrates that may be placed on another object (e.g., a stand).

The material of the substrate includes metals, resins, glass, sapphire, ceramics, stone, and composite materials of these. The glass may be chemically strengthened. An underlayer film such as a $SiO_2$ film may be formed on the surface of the substrate.

As the substrate, a substrate for a touch panel, a substrate for a display, and a spectacle lens is preferred, and a substrate for a touch panel is particularly preferred. As the material of a substrate for a touch panel, glass or transparent resin is preferred.

Further, as the substrate, glass or resin film used for the exterior portion (excluding the display unit) in devices such as mobile phones (e.g., smartphones), portable information terminals (e.g., tablet terminals), game consoles, remote controls, and the like is also preferred.

Method for Producing Article

The present article can be produced, for example, by the following methods.

- A method of treating the surface of the substrate by a dry coating method using the present compound or the present composition to form a surface layer formed from the present compound or the present composition on the surface of the substrate.
- A method of applying the present coating liquid onto the surface of the substrate by a wet coating method and drying to form a surface layer formed from the present compound or the present composition on the surface of the substrate.

Examples of the dry coating method include methods such as vacuum deposition, CVD, and sputtering. As the dry coating method, a vacuum deposition method is preferred from the perspective of suppressing the decomposition of compound (A1) or compound (B1) and from the perspective of ease of use of the apparatus. During vacuum deposition, a pellet-like substance impregnated with the present compound or the present composition in a metal porous body of iron, steel, or the like may be used. A pellet-like substance in which compound (A1) or compound (B1), or the present composition is impregnated may be used, which is obtained by impregnating a metal porous body of iron, steel, or the like with the present coating liquid, and drying the liquid.

Examples of the wet coating method include spin coating, wipe coating, spray coating, squeegee coating, dip coating, die coating, an inkjet method, flow coating, roll coating, casting, a Langmuir-Blodgett method, and gravure coating.

In order to improve the abrasion resistance of the surface layer, an operation may be performed as necessary to promote the reaction between the present compound and the substrate. Examples of the operation include heating, humidification, light irradiation, and the like.

For example, the substrate on which the surface layer is formed may be heated in an atmosphere having moisture to promote reactions, such as a hydrolysis reaction of hydrolyzable groups, a reaction between hydroxyl groups and the like on the surface of the substrate and silanol groups, and generation of siloxane bonds by a condensation reaction of silanol groups.

After the surface treatment, compounds in the surface layer that are not chemically bonded to another compound or the substrate may be removed as necessary. Specific methods include, for example, a method of pouring a solvent on the surface layer, a method of wiping off with a cloth soaked with a solvent, and the like.

EXAMPLES

The present invention will now be described in more detail using the following examples, but the present invention is not limited to these examples. In the following, unless otherwise noted, "%" means "% by mass". Examples 1 to 11, 13 to 33, and 35 to 41 are examples, and Examples 12 and 34 are comparative examples.

The weight average molecular weight (Mw)/number average molecular weight (Mn) was obtained by GPC (gel penetration chromatography) under the following conditions.

Apparatus: HLC-8420GPC (Manufactured by Tosoh Corporation)

Mobile phase: Mixed solvent of 1,3-bis(trifluoromethyl) benzene and acetone (80:20 (volume ratio))

Analysis column: PLgel 3 μm MIXED-E (Agilent Technologies)

Standard sample for molecular weight measurement: Three kinds of perfluoropolyether having a Mw/Mn of 1.2 or less, and an Mn from 2000 to 10000 Mobile phase flow velocity: 1.0 mL/min Sample concentration: 10 mg/mL Column temperature: 40° C.

Detector: Evaporative light scattering detector

Synthesis Example 1: Synthesis of Compound (1-1)

The following compound (1-1) was obtained according to the method described in Example 7 of International Patent Publication No. WO 2013/121984.

Formula (1-1)

$$CF_3—O—(CF_2CF_2OCF_2CF_2CF_2CF_2O)_n(CF_2CF_2O)—CF_2CF_2CF_2CH_2OH$$

The average value of the repeating unit number n is 13.

Synthesis Example 2: Synthesis of Compound (1-2)

Compound (1-1) (6.80 g), 2,6-lutidine (0.759 g), and AE-3000 (28.0 g) were added and stirred at 0° C. Trifluoromethane sulfonate anhydride (0.987 g) was added, and the mixture was then stirred at room temperature. After washing with water, the solvent was removed by distillation, and flash column chromatography using silica gel was carried out to obtain 6.81 g of the following compound (1-2).

Formula (1-2)

$$CF_3-O-(CF_2CF_2OCF_2CF_2CF_2CF_2O)_n(CF_2CF_2O)-CF_2CF_2CF_2CH_2OTf$$

The average value of the repeating unit number n is 13, and OTf is triflate: —O—S(=O)$_2$(—$CF_3$).

NMR spectrum of compound (1-2):

$^1$H-NMR (400 MHz, Chloroform-d) δ (ppm): 4.78 (t, J=12.3 Hz, 2H).

$^{19}$F-NMR (376 MHz, Chloroform-d) δ (ppm): −55.28, −74.11, −82.86, −88.07, −90.20, −119.84, −125.28, −126.16.

Synthesis Example 3: Synthesis of Compound (B-1)

Diethyl diallylmalonate (60.0 g), lithium chloride (23.7 g), water (6.45 g), and dimethyl sulfoxide (263 g) were added and stirred at 160° C. After cooling to room temperature, water was added and extraction was carried out with ethyl acetate. Hexane was added to the organic layer, which was then washed with saturated saline, and dried over sodium sulfate. After filtration, the solvent was removed by distillation to obtain 39.5 g of the following compound (B-1).

[Formula 6]

Formula (B-1)

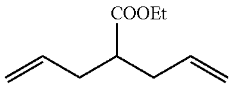

NMR spectrum of compound (B-1):

$^1$H-NMR (400 MHz, Chloroform-d) δ (ppm): (ddt, J=17.1, 10.1, 7.0 Hz, 2H), 5.06-4.94 (m, 4H), 4.09 (q, J=7.1 Hz, 2H), 2.47 (ddd, J=14.0, 8.0, 6.1 Hz, 1H), 2.33 (dt, J=14.9, 7.5 Hz, 2H), 2.22 (dt, J=14.1, 6.5 Hz, 2H), 1.21 (t, J=7.1 Hz, 3H).

Synthesis Example 4: Synthesis of Compound (B-2)

Tetrahydrofuran (THF) (260 mL), diisopropylamine (29.8 g) were added, the solution was then cooled to −78° C. A solution of n-butyl lithium in hexane (2.76 M, 96.6 mL) was added, and the temperature was raised to 0° C. After stirring, the solution was cooled to −78° C. to prepare a solution of lithium diisopropylamide (LDA) in THF. Compound (B-1) (39.5 g) was added to the THF solution, and after stirring, allyl bromide (24.1 mL) was added. The temperature was raised to 0° C., 1 M hydrochloric acid (100 mL) was added, and THF was removed by distillation under reduced pressure. After extraction with dichloromethane, sodium sulfate was added. After filtration, the solvent was removed by distillation, and flash column chromatography using silica gel was carried out to obtain 45.0 g of compound (B-2).

[Formula 7]

Formula (B-2)

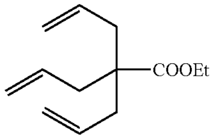

NMR spectrum of compound (B-2):

$^1$H-NMR (400 MHz, Chloroform-d) δ (ppm): 5.74-5.62 (m, 3H), 5.04 (dd, J=13.6, 1.9 Hz, 6H), 4.10 (q, J=7.1 Hz, 2H), 2.29 (d, J=7.4 Hz, 6H), 1.22 (t, J=7.1 Hz, 3H).

Synthesis Example 5: Synthesis of Compound (B-3)

Compound (B-2) (45.0 g) was dissolved in THF (620 mL) and cooled to 0° C. A solution of lithium aluminum hydride in THF (104 mL) was added, and the mixture was stirred. Water and an aqueous solution of 15% sodium hydroxide were added, the mixture was stirred at room temperature, and then diluted with dichloromethane. After filtration, the solvent was removed by distillation, and flash column chromatography using silica gel was carried out to obtain 31.3 g of the following compound (B-3).

[Formula 8]

Formula (B-3)

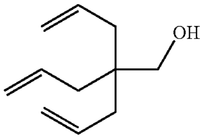

NMR spectrum of compound (B-3):

$^1$H-NMR (400 MHz, Chloroform-d) δ (ppm): 5.90-5.76 (m, 3H), 5.10-5.02 (m, 6H), 3.38 (s, 2H), 2.03 (dt, J=7.5, 1.2 Hz, 6H), 1.45 (s, 1H).

Example 1: Synthesis of Compound (B1-1)

Acetonitrile (380 mL), compound (B-3) (31.3 g), triphenylphosphine (64.3 g), and carbon tetrachloride (33.9 g) were added and stirred at 90° C. After concentration, ethyl acetate/hexane was added and the mixture was stirred. After filtration and concentration, distillation was carried out to obtain 28.2 g of the following compound (B1-1).

[Formula 9]

Formula (B1-1)

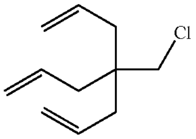

NMR spectrum of compound (B1-1):

$^{1}$H-NMR (400 MHz, Chloroform-d) δ (ppm): 5.83-5.67 (m, 3H), 5.16-5.01 (m, 6H), 3.32 (s, 2H), 2.05 (dt, J=7.5, 1.1 Hz, 6H).

Example 2: Synthesis of Compound (B2-1)

THF (35 mL) and iodine (0.180 g) were added to magnesium (2.36 g), and the mixture was stirred at room temperature. A solution of compound (B1-1) (14.0 g) in THF (35 mL) was added, and the mixture was heated to reflux for 2 hours to prepare a solution (0.80 M) of the following compound (B2-1).

[Formula 10]

Formula (B2-1)

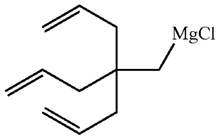

Example 3: Synthesis of Compound (B1-2)

1-Bromo-3-chloropropane (2.90 g), 1-phenyl-1-propyne (0.220 g), and $CuCl_2$ (0.051 g) were added and stirred at 0° C. Compound (B2-1) (0.80 M, 26.0 mL) was added, and the mixture was stirred. 1 M hydrochloric acid was added, extraction was carried out with dichloromethane, and sodium sulfate was added. After filtration and concentration, distillation was carried out to obtain 3.29 g of the following compound (B1-2).

[Formula 11]

Formula (B1-2)

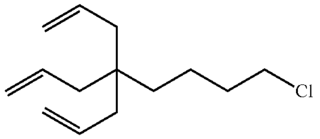

NMR spectrum of compound (B1-2):

$^{1}$H-NMR (400 MHz, Chloroform-d) δ (ppm): 5.76 (ddt, J=16.6, 10.6, 7.4 Hz, 3H), 5.09-4.93 (m, 6H), 3.50 (t, J=6.7 Hz, 2H), 1.96 (dt, J=7.4, 1.2 Hz, 6H), 1.76-1.61 (m, 2H), 1.45-1.29 (m, 2H), 1.24-1.08 (m, 2H).

Example 4: Synthesis of Compound (B2-2)

THF (2.6 mL) and iodine (12.7 mg) were added to magnesium (0.174 g) and the mixture was stirred at room temperature. A solution of compound (B1-2) (1.30 g) in THF (2.6 mL) was added, and the mixture was heated to reflux to prepare a solution (1.0 M) of the following compound (B2-2).

[Formula 12]

Formula (B2-2)

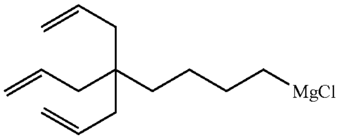

Synthesis Example 6: Synthesis of Compound (1-3)

$CuCl_2$ (7.0 mg), 1-phenyl-1-propyne (0.026 g), 1,3-bis-trifluoromethylbenzene (23 mL), and compound (1-2) (1.52 g) were added, and then compound (B2-2) (4.5 mL, 1.0 M) was added. After stirring at room temperature, the mixture was washed with 1 M hydrochloric acid and dried over sodium sulfate. After filtration, the solvent was removed by distillation and AC-6000 was added. After washing with N,N-dimethylformamide (DMF), flash column chromatography using silica gel was carried out to obtain 0.210 g of the following compound (1-3).

[Formula 13]

Compound (1-3)

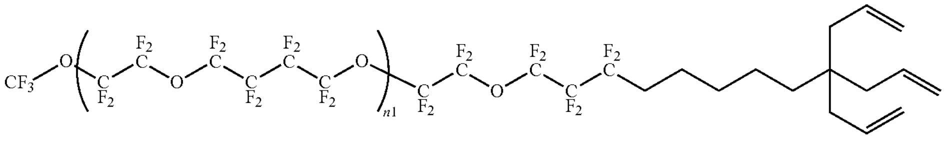

NMR spectrum of compound (1-3):

$^{1}$H-NMR (400 MHz, Chloroform-d) δ (ppm): 5.80 (ddt, J=20.3, 9.3, 7.4 Hz, 3H), 5.01 (dd, J=13.5, 1.7 Hz, 6H), 2.13-2.01 (m, 2H), 1.97 (d, J=7.5 Hz, 6H), 1.67-1.55 (m, 2H), 1.40-1.27 (m, 4H), 1.27-1.18 (m, 2H).

$^{19}$F-NMR (376 MHz, Chloroform-d) δ (ppm): −55.25, −82.83, −88.06, −90.16 (d, J=8.1 Hz), −114.18, −125.26, −126.59.

Example 5: Synthesis of Compound (I)

AC-2000 (1.2 g), compound (1-3) (0.200 g), a solution of a platinum/1,3-divinyl-1,1,3,3-tetramethyl disiloxane complex (platinum content 2%, 7.0 mg) in xylene, aniline (1.5 mg), and trimethoxysilane (32.2 mg) were added, the mixture was stirred at 40° C. for 18 hours, and then the solvent was removed by distillation under reduced pressure to obtain 0.201 g of the fluorine-containing ether compound (I) shown below. The Mw/Mn of compound (I) calculated by the GPC method was 1.07.

[Formula 14]

Compound (I)

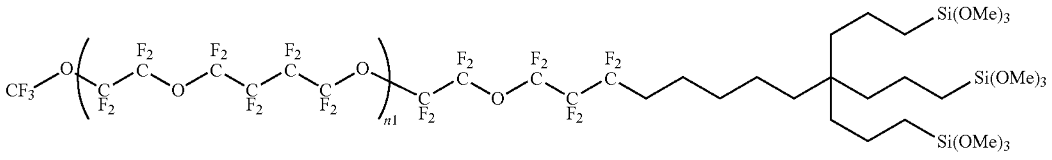

Average value (n1) of repeating units: 13

NMR spectrum of compound (I):

$^{1}$H-NMR (400 MHz, Chloroform-d) δ (ppm): 3.59 (s, 27H), 2.15-1.91 (m, 2H), 1.72-1.54 (m, 2H), 1.52-1.14 (m, 18H), 0.73-0.60 (m, 6H).

$^{19}$F-NMR (376 MHz, Chloroform-d) δ (ppm): −55.28, −82.30 (d, J=22.0 Hz), −82.88, −88.10, −90.22, −114.17, −125.30, −126.49.

Example 6: Synthesis of Compound (B1-3)

1-Bromo-4-chlorobutane (2.89 g), 1-phenyl-1-propyne (0.198 g), and $CuCl_2$ (0.049 g) were added and stirred at 0° C. Compound (B2-1) (0.80 M, 24.0 mL) was added, and the mixture was stirred. 1 M hydrochloric acid was added, extraction was carried out with dichloromethane, and sodium sulfate was added. After filtration and concentration, distillation was carried out to obtain 3.45 g of the following compound (B1-3).

[Formula 15]

Formula (B1-3)

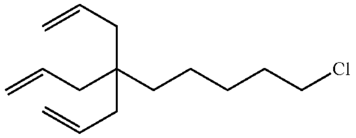

[Formula 16]

Formula (B2-3)

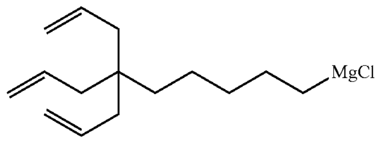

Synthesis Example 7: Synthesis of Compound (2-1)

$CuCl_2$ (9.9 mg), 1-phenyl-1-propyne (0.019 g), 1,3-bis-trifluoromethylbenzene (23 mL), and compound (1-2) (1.50 g) were added, and then compound (B2-3) (4.5 mL, 1.0 M) was added. After stirring at room temperature, the mixture was washed with 1 M hydrochloric acid and dried over sodium sulfate. After filtration, the solvent was removed by distillation and AC-6000 was added. After washing with DMF and MeOH, flash column chromatography using silica gel was carried out to obtain 0.246 g of the following compound (2-1).

[Formula 17]

Compound (2-1)

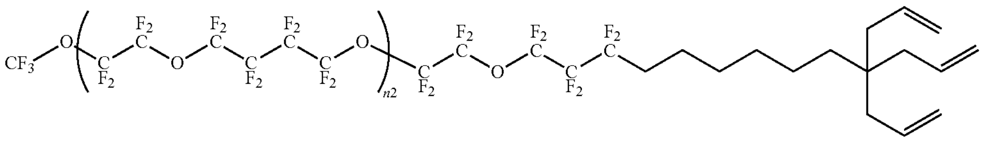

NMR spectrum of compound (B1-3):

$^{1}$H-NMR (400 MHz, Chloroform-d) δ (ppm): 5.76 (ddt, J=16.8, 10.4, 7.4 Hz, 3H), 5.07-4.92 (m, 6H), 3.49 (t, J=6.8 Hz, 2H), 1.94 (dt, J=7.4, 1.2 Hz, 6H), 1.79-1.67 (m, 2H), 1.42-1.30 (m, 2H), 1.30-1.20 (m, 2H), 1.20-1.10 (m, 2H).

Example 7: Synthesis of Compound (B2-3)

THF (2.6 mL) and iodine (14.0 mg) were added to magnesium (0.168 g), and the mixture was stirred at room temperature. A solution of compound (B1-3) (1.41 g) in THF (2.6 mL) was added, and the mixture was heated to reflux for 2 hours to prepare a solution (0.74 M) of the following compound (B2-3).

NMR spectrum of compound (2-1):

$^{1}$H-NMR (400 MHz, Chloroform-d) δ (ppm): 5.90-5.73 (m, 3H), 5.13-4.91 (m, 6H), 2.14-2.01 (m, 2H), 1.97 (d, J=7.4 Hz, 6H), 1.69-1.52 (m, 2H), 1.47-1.18 (m, 8H).

$^{19}$F-NMR (376 MHz, Chloroform-d) δ (ppm): −55.23, −82.35 (dt, J=22.8, 10.3 Hz), −82.81, −87.93, −90.15 (d, J=8.4 Hz), −114.19, −125.23, −126.58.

Example 8: Synthesis of Compound (II)

AC-2000 (1.5 g), compound (2-1) (0.246 g), a solution of a platinum/1,3-divinyl-1,1,3,3-tetramethyl disiloxane complex (platinum content 2%, 8.9 mg) in xylene, aniline (1.3 mg), and trimethoxysilane (26.9 mg) were added, the mixture was stirred at 40° C., and then the solvent was removed by distillation under reduced pressure to obtain 0.252 g of the fluorine-containing ether compound (II) shown below. The Mw/Mn of compound (II) calculated by the GPC method was 1.06.

[Formula 18]

Compound (II)

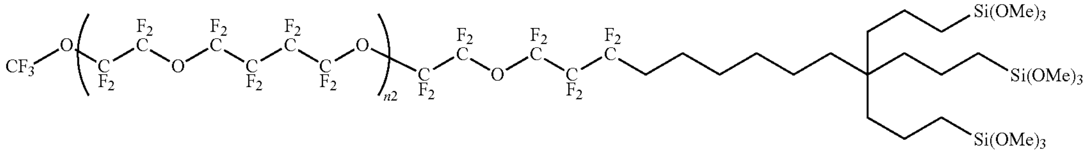

Average value (n2) of repeating units: 14

NMR spectrum of compound (II):

$^1$H-NMR (400 MHz, Chloroform-d) δ (ppm): 3.60 (s, 27H), 2.14-1.95 (m, 2H), 1.66-1.54 (m, 2H), 1.52-1.16 (m, 20H), 0.75-0.61 (m, 6H).

$^{19}$F-NMR (376 MHz, Chloroform-d) δ (ppm): −55.28, −82.33, −82.86, −88.08, −90.18, −114.24, −125.29, −126.51.

Example 9: Synthesis of Compound (B1-4)

1-Bromo-5-chlorobutane (2.89 g), 1-phenyl-1-propyne (0.182 g), and $CuCl_2$ (0.042 g) were added and stirred at 0° C. Compound (B2-1) (0.80 M, 21.5 mL) was added, and the mixture was stirred for 1 hour. 1 M hydrochloric acid was added, extraction was carried out with dichloromethane, and sodium sulfate was added. After filtration and concentration, flash column chromatography using silica gel was carried out to obtain 2.95 g of the following compound (B1-4).

[Formula 19]

Formula (B1-4)

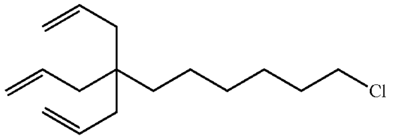

NMR spectrum of compound (B1-4):

$^1$H-NMR (400 MHz, Chloroform-d) δ (ppm): 5.83-5.68 (m, 3H), 5.06-4.94 (m, 6H), 3.49 (t, J=6.8 Hz, 2H), 1.94 (dt, J=7.4, 1.2 Hz, 6H), 1.80-1.65 (m, 2H), 1.46-1.32 (m, 2H), 1.28-1.09 (m, 6H).

Example 10: Synthesis of Compound (B2-4)

THF (2.6 mL) and iodine (21.8 mg) were added to magnesium (0.172 g), and the mixture was stirred at room temperature. A solution of compound (B1-4) (1.47 g) in THF (2.6 mL) was added, and the mixture was heated to reflux for 2 hours to prepare a solution (0.99 M) of the following compound (B2-4).

[Formula 20]

Formula (B2-4)

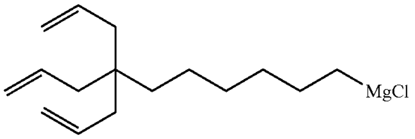

Synthesis Example 8: Synthesis of Compound (3-1)

$CuCl_2$ (7.0 mg), 1-phenyl-1-propyne (0.026 g), 1,3-bis-trifluoromethylbenzene (24 mL), and compound (1-2) (1.51 g) were added, and then compound (B2-4) (4.8 mL, 0.99 M) was added. After stirring at room temperature, the mixture was washed with 1 M hydrochloric acid and dried over sodium sulfate. After filtration, the solvent was removed by distillation, washed with hexane, and flash column chromatography using silica gel was carried out to obtain 0.213 g of the following compound (3-1).

[Formula 21]

Compound (3-1)

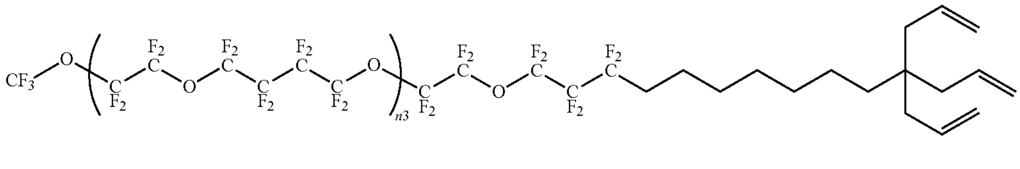

NMR spectrum of compound (3-1):

$^1$H-NMR (400 MHz, Chloroform-d) δ (ppm): 5.87-5.72 (m, 3H), 5.07-4.93 (m, 6H), 2.12-1.99 (m, 2H), 1.97 (d, J=7.5 Hz, 6H), 1.64-1.53 (m, 2H), 1.41-1.17 (m, 10H).

$^{19}$F-NMR (376 MHz, Chloroform-d) δ (ppm): −55.22, −82.77, −87.95 (d, J=39.1 Hz), −90.12 (d, J=8.5 Hz), −114.15, −125.19, −126.55.

Example 11: Synthesis of Compound (111)

AC-2000 (1.3 g), compound (1-7) (0.213 g), a solution of a platinum/1,3-divinyl-1,1,3,3-tetramethyl disiloxane complex (platinum content 2%, 7.4 mg) in xylene, aniline (2.2 mg), and trimethoxysilane (45.9 mg) were added, the mixture was stirred at 40° C., and then the solvent was removed by distillation under reduced pressure to obtain 0.225 g of the fluorine-containing ether compound (III) shown below. The Mw/Mn of compound (III) calculated by the GPC method was 1.07.

[Formula 22]

Compound (III)

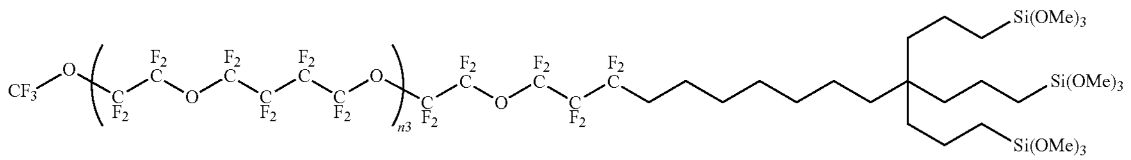

Average value (n3) of repeating units: 13

NMR spectrum of compound (III):

$^1$H-NMR (400 MHz, Chloroform-d) δ (ppm): 3.60 (s, 27H), 2.15-1.94 (m, 2H), 1.66-1.54 (m, 2H), 1.54-1.13 (m, 22H), 0.75-0.61 (m, 6H).

$^{19}$F-NMR (376 MHz, Chloroform-d) δ (ppm): −55.26, −82.32 (dt, J=23.2, 10.6 Hz), −82.84, −88.07, −90.17 (d, J=8.6 Hz), −114.18, −125.24 (d, J=16.1 Hz), −126.51.

Example 12: Synthesis of Compound (IV)

The following compound (IV) was obtained according to the method described in Example 7 of International Patent Publication No. WO 2017/038830.

Formula (IV)

$$CF_3—O—(CF_2CF_2O—CF_2CF_2CF_2CF_2O)_{n4}(CF_2CF_2O)—CF_2CF_2CF_2—CH_2OCH_2—C\{CH_2CH_2CH_2Si(OMe)_3)\}_3$$

The average value of the repeating unit number n4 is 13.

Synthesis Example 9: Synthesis of Compound (5-1)

$CuCl_2$ (16.0 mg), 1-phenyl-1-propyne (0.052 g), 1,3-bistrifluoromethylbenzene (24 mL), and compound (1-2) (4.00 g) were added, and then compound (B2-1) (5.0 mL, 1.0 M) was added. After stirring at room temperature, the mixture was washed with 1 M hydrochloric acid and dried over sodium sulfate. After filtration, the solvent was removed by distillation and AC-6000 was added. After washing with MeOH, flash column chromatography using silica gel was carried out to obtain 0.139 g of the following compound (5-1).

[Formula 23]

Compound (5-1)

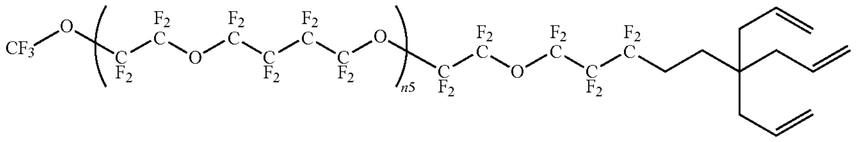

Average value (n5) of repeating units: 10

NMR spectrum of compound (5-1):

$^{1}$H-NMR (400 MHz, Chloroform-d) δ (ppm): 5.77 (ddt, J=14.9, 10.7, 7.4 Hz, 3H), 5.07-4.99 (m, 6H), 2.19-2.05 (m, 2H), 1.97 (d, J=7.4 Hz, 6H), 1.59-1.50 (m, 2H).

$^{19}$F-NMR (376 MHz, Chloroform-d) δ (ppm): −55.29, −82.90, −88.13, −90.24 (d, J=8.0 Hz), −114.62, −125.34, −126.49.

Example 13: Synthesis of Compound (V)

AC-2000 (0.89 g), compound (5-1) (0.139 g), a solution of a platinum/1,3-divinyl-1,1,3,3-tetramethyl disiloxane complex (platinum content 2%, 5.5 mg) in xylene, aniline (0.8 mg), and trimethoxysilane (22.7 mg) were added, the mixture was stirred at 40° C., and then the solvent was removed by distillation under reduced pressure to obtain 0.145 g of the following fluorine-containing ether compound (V). The Mw/Mn of compound (V) calculated by the GPC method was 1.07.

[Formula 25]

Formula (B1-5)

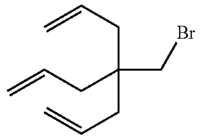

NMR spectrum of compound (B1-5):

$^{1}$H-NMR (400 MHz, Chloroform-d) δ (ppm): 5.74 (ddt, J=16.7, 10.5, 7.5 Hz, 3H), 5.18-5.01 (m, 6H), 3.24 (s, 2H), 2.06 (dt, J=7.5, 1.1 Hz, 6H).

The fact that compound (V) can be synthesized was confirmed by performing the same procedures as in Example 2, Synthesis Example 9, and Example 13, except that compound (B1-5) was used instead of compound (B1-1).

Synthetic Example 10: Synthesis of Compound (B-4)

Paraformaldehyde (0.489 g) and THF (9.5 mL) were added, and then compound (B2-1) (20 mL, 0.9 M) was added. After stirring at room temperature, 1 M hydrochloric acid was added. The mixture was extracted with dichloromethane, and then dried over sodium sulfate. After filtration, the solvent was removed by distillation, and flash column chromatography using silica gel was carried out to obtain 1.98 g of the following compound (hydroxide form).

[Formula 24]

Compound (V)

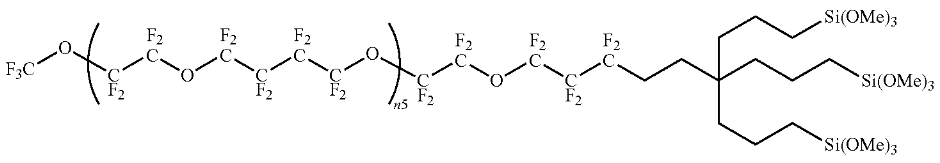

Average value (n5) of repeating units: 10

NMR spectrum of compound (V):

$^{1}$H-NMR (400 MHz, Chloroform-d) δ (ppm): 3.60 (s, 27H), 2.23-1.95 (m, 2H), 1.63-1.28 (m, 14H), 0.67 (t, J=7.6 Hz, 6H).

$^{19}$F-NMR (376 MHz, Chloroform-d) δ (ppm): −55.33, −82.95, −88.17, −90.13−−90.40 (m), −114.07−−114.32 (m), −125.38, −126.04.

Example 14: Synthesis of Compound (B1-5)

THF (33 mL), compound (B-3) (1.66 g), triphenylphosphine (2.88 g), and carbon tetrabromide (3.64 g) were added and stirred at 10° C. Hexane (30 mL) was added, and after filtration and concentration, distillation was carried out to obtain 1.06 g of the following compound (B1-5).

[Formula 26]

Formula (B-4)

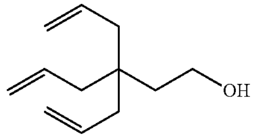

NMR spectrum of compound (B-4):

$^1$H-NMR (400 MHz, Chloroform-d) δ (ppm): 5.80 (ddt, J=16.8, 10.4, 7.4 Hz, 3H), 5.14-4.91 (m, 6H), 3.74-3.60 (m, 2H), 1.99 (dt, J=7.4, 1.2 Hz, 6H), 1.61-1.45 (m, 2H).

Example 15: Synthesis of Compound (B1-6)

Acetonitrile (22 mL), compound (2-3) (1.98 g), triphenylphosphine (3.75 g), and carbon tetrachloride (2.00 g) were added and stirred at 90° C. After concentration, ethyl acetate/hexane was added and the mixture was stirred. After filtration and concentration, flash column chromatography using silica gel was carried out to obtain 1.73 g of the following compound (B1-6).

[Formula 27]

Formula (B1-6)

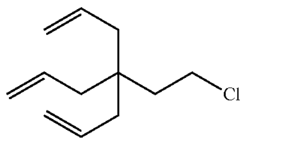

NMR spectrum of compound (B1-6):

$^1$H-NMR (400 MHz, Chloroform-d) δ (ppm): 5.84-5.69 (m, 3H), 5.12-4.98 (m, 6H), 3.55-3.46 (m, 2H), 1.98 (dt, J=7.4, 1.2 Hz, 6H), 1.76-1.68 (m, 2H).

Example 16: Synthesis of Compound (B2-6)

THF (1.3 mL) and iodine (9.0 mg) were added to magnesium (0.099 g) and the mixture was stirred at room temperature. A solution of compound (B1-6) (0.570 g) in THF (1.3 mL) was added, and the mixture was heated to reflux to prepare a solution (1.0 M) of the following compound (B2-6).

[Formula 28]

Formula (B2-6)

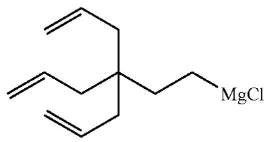

Synthesis Example 11: Synthesis of Compound (6-1)

$CuCl_2$ (4.0 mg), 1-phenyl-1-propyne (0.116 g), 1,3-bistrifluoromethylbenzene (10 mL), and compound (1-2) (1.01 g) were added, and then compound (B2-6) (1.6 mL, 1.0 M) was added. After stirring at room temperature, the mixture was washed with 1 M hydrochloric acid and dried over sodium sulfate. After filtration, the solvent was removed by distillation and AC-6000 was added. After washing with MeOH, flash column chromatography using silica gel was carried out to obtain 0.110 g of the following compound (6-1).

[Formula 29]

Compound (6-1)

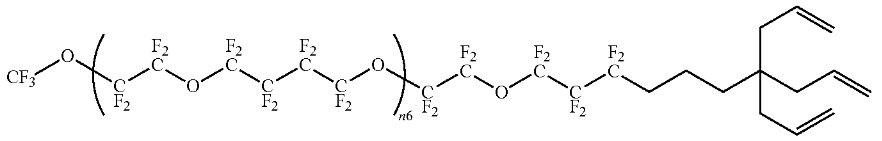

Average value (n6) of repeating units: 11

NMR spectrum of compound (6-1):

$^1$H-NMR (400 MHz, Chloroform-d) δ (ppm): 5.85-5.71 (m, 3H), 5.07-4.94 (m, 6H), 2.04-1.78 (m, 8H), 1.64-1.38 (m, 2H), 1.32-1.05 (m, 2H).

$^{19}$F-NMR (376 MHz, Chloroform-d) δ (ppm): −55.28, −82.40, −82.86, −88.09, −90.20 (d, J=9.6 Hz), −114.25, −125.29, −126.55.

Example 17: Synthesis of Compound (VI)

AC-2000 (0.89 g), compound (6-1) (0.110 g), a solution of a platinum/1,3-divinyl-1,1,3,3-tetramethyl disiloxane complex (platinum content 2%, 5.3 mg) in xylene, aniline (0.9 mg), and trimethoxysilane (22.7 mg) were added, the mixture was stirred at 40° C., and then the solvent was removed by distillation under reduced pressure to obtain 0.109 g of the following fluorine-containing ether compound (VI). The Mw/Mn of compound (VI) calculated by the GPC method was 1.08.

[Formula 30]

Compound (VI)

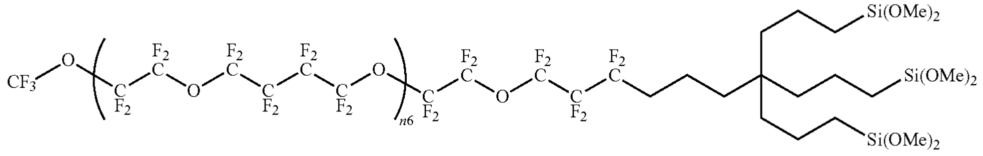

Average value (n6) of repeating units: 11

NMR spectrum of compound (VI):

$^{1}$H-NMR (400 MHz, Chloroform-d) δ (ppm): 3.58 (s, 27H), 2.23-1.98 (m, 2H), 1.64-1.20 (m, 16H), 0.79-0.58 (m, 6H).

$^{19}$F-NMR (376 MHz, Chloroform-d) δ (ppm): −55.28, −82.90, −88.13, −90.11−−90.30 (m), −114.01−−114.29 (m), −125.31, −125.99.

Example 18: Synthesis of Compound (B1-7)

THF (44 mL), compound (B-3) (4.00 g), triphenylphosphine (7.64 g), and carbon tetrabromide (8.66 g) were added and stirred at 0° C. Hexane (10 mL) was added, and after filtration and concentration, flash column chromatography using silica gel was carried out to obtain 3.36 g of the following compound (B1-7).

[Formula 31]

Formula (B1-7)

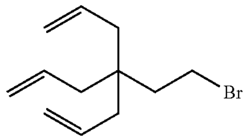

NMR spectrum of compound (B1-7):

$^{1}$H-NMR (400 MHz, Chloroform-d) δ (ppm): 5.79 (ddt, J=16.8, 10.2, 7.4 Hz, 3H), 5.18-4.98 (m, 6H), 3.48-3.29 (m, 2H), 2.05-1.93 (m, 6H), 1.89-1.78 (m, 2H).

The fact that Compound (VI) can be synthesized was confirmed by performing the same procedures as in Example 16, Synthesis Example 11, and Example 17, except that compound (B1-7) was used instead of compound (B1-6).

Example 19: Synthesis of Compound (B1-8)

1-Bromo-2-chloroethane (2.90 g), 1-phenyl-1-propyne (0.235 g), and $CuCl_2$ (0.055 g) were added and stirred at 0° C. Compound (B2-1) (0.97 M, 7.0 mL) was added, and the mixture was stirred for 1 hour. 1 M hydrochloric acid was added, extraction was carried out with dichloromethane, and sodium sulfate was added. After filtration and concentration, distillation was carried out to obtain 2.32 g of the following compound (B1-8).

[Formula 32]

Formula (B1-8)

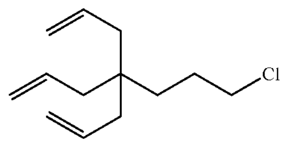

NMR spectrum of compound (B1-8).

$^{1}$H-NMR (400 MHz, Chloroform-d) δ (ppm): 5.77 (ddt, J=16.8, 10.4, 7.4 Hz, 3H), 5.07-4.96 (m, 6H), 3.45 (t, J=6.7 Hz, 2H), 1.96 (dt, J=7.4, 1.2 Hz, 6H), 1.78-1.65 (m, 2H), 1.33-1.24 (m, 2H).

Example 20: Synthesis of Compound (B2-8)

THF (2.6 mL) and iodine (0.013 g) were added to magnesium (0.174 g) and the mixture was stirred at room temperature. A solution of compound (B1-8) (1.21 g) in THF (2.6 mL) was added, and the mixture was heated to reflux to prepare a solution (1.0 M) of the following compound (B2-8).

[Formula 33]

Formula (B2-8)

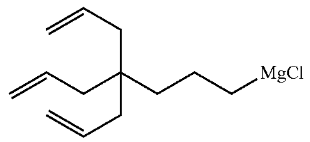

Synthesis Example 12: Synthesis of Compound (7-1)

$CuCl_2$ (6.4 mg), 1-phenyl-1-propyne (0.018 g), 1,3-bis-trifluoromethylbenzene (23 mL), and compound (1-2) (1.50 g) were added, and then compound (B2-8) (4.5 mL, 1.0 M) was added. After stirring at room temperature, the mixture was washed with 1 M hydrochloric acid and dried over sodium sulfate. After filtration, the solvent was removed by distillation and AC-6000 was added. After washing with MeOH, flash column chromatography using silica gel was carried out to obtain 0.126 g of the following compound (7-1).

[Formula 34]

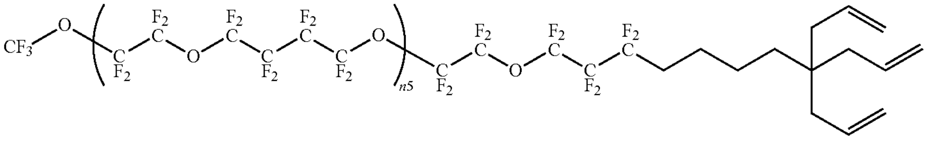

Compound (7-1)

Average value (n7) of repeating units: 12

NMR spectrum of compound (7-1):

$^1$H-NMR (400 MHz, Chloroform-d) δ (ppm): 5.87-5.68 (m, 3H), 5.06-4.92 (m, 6H), 2.16-1.92 (m, 8H), 1.62-1.50 (m, 2H), 1.41-1.34 (m, 2H), 1.28-1.19 (m, 2H)

$^{19}$F-NMR (376 MHz, Chloroform-d) δ (ppm): −55.23, −82.33, −82.78, −88.02, −90.15, −114.17, −125.21, −126.55.

Example 21: Synthesis of Compound (VII)

AC-2000 (0.89 g), compound (7-1) (0.126 g), a solution of a platinum/1,3-divinyl-1,1,3,3-tetramethyl disiloxane complex (platinum content 2%, 5.5 mg) in xylene, aniline (1.8 mg), and trimethoxysilane (22.7 mg) were added, the mixture was stirred at 40° C., and then the solvent was removed by distillation under reduced pressure to obtain 0.111 g of the following fluorine-containing ether compound (VII). The Mw/Mn of compound (VII) calculated by the GPC method was 1.07.

[Formula 35]

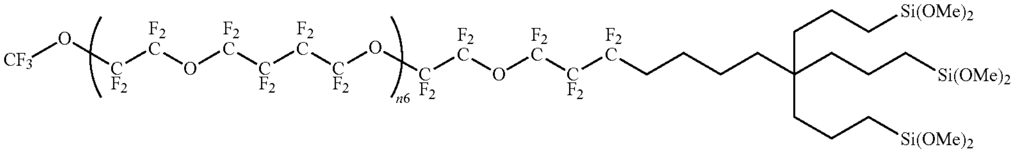

Compound (VII)

Average value (n7) of repeating units: 12

NMR spectrum of compound (VII):

$^1$H-NMR (400 MHz, Chloroform-d) δ (ppm): 3.59 (s, 27H), 2.18-1.93 (m, 2H), 1.70-1.19 (m, 18H), 0.77-0.61 (m, 6H).

$^{19}$F-NMR (376 MHz, Chloroform-d) δ (ppm): −55.28, −82.60 (d, J=22.0 Hz), −82.78, −88.11, −90.21, −114.11, −125.32, −126.11.

Synthesis Example 13: Synthesis of Compound (8-1)

FLUOROLINK D4000 (manufactured by Solvay Specialty Polymers) (4.03 g), 2,6-lutidine (0.759 g), and AE-3000 (28.0 g) were added and stirred at 0° C. Trifluoromethane sulfonate anhydride (0.987 g) was added, and the mixture was then stirred at room temperature. After washing with water, the solvent was removed by distillation, and flash column chromatography using silica gel was carried out to obtain 3.56 g of the following compound (8-1).

[Formula 36]

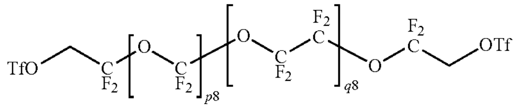

Compound (8-1)

Average value of p8: 22, average value of q8: 25

NMR spectrum of compound (8-1):

$^1$H-NMR (400 MHz, Chloroform-d) δ (ppm): 4.89 (q, J=8.4 Hz, 1H).

Synthesis Example 14: Synthesis of Compound (8-2)

$CuCl_2$ (7.0 mg), 1-phenyl-1-propyne (0.026 g), 1,3-bis-trifluoromethylbenzene (15 mL), and compound (8-1) (1.62 g) were added, and then compound (B1-2) (4.0 mL, 1.0 M) was added. After stirring at room temperature, the mixture was washed with 1 M hydrochloric acid and dried over sodium sulfate. After filtration, the solvent was removed by distillation and AC-6000 was added. After washing with methanol, flash column chromatography using silica gel was carried out to obtain 0.201 g of the following compound (8-2).

[Formula 37]

Compound (8-2)

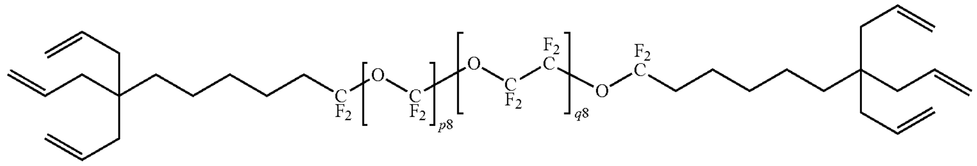

Average value of p8: 22, average value of q8: 25

NMR spectrum of compound (8-2):

$^1$H-NMR (400 MHz, Chloroform-d) δ (ppm): 5.90-5.66 (m, 6H), 5.07-4.90 (m, 12H), 2.19-1.92 (m, 16H), 1.70-1.10 (m, 16H).

Example 21: Synthesis of Compound (VIII)

AC-2000 (1.2 g), compound (8-2) (0.201 g), a solution of a platinum/1,3-divinyl-1,1,3,3-tetramethyl disiloxane complex (platinum content 2%, 7.0 mg) in xylene, aniline (1.4 mg), and trimethoxysilane (51.7 mg) were added, the mixture was stirred at 40° C. for 18 hours, and then the solvent was removed by distillation under reduced pressure to obtain 0.188 g of the following fluorine-containing ether compound (VIII). The Mw/Mn of compound (VIII) calculated by the GPC method was 1.11.

[Formula 38]

Compound (VIII)

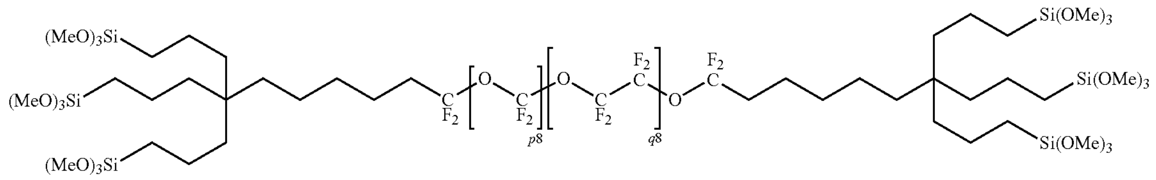

Average value of p8: 22, average value of q8: 25

NMR spectrum of compound (VIII):

$^1$H-NMR (400 MHz, Chloroform-d) δ (ppm): 3.61 (s, 54H), 2.17-1.90 (m, 4H), 1.70-1.14 (m, 40H), 0.74-0.59 (m, 12H).

Synthetic Example 15: Synthesis of Compound (9-1)

The following compound (9-1) was synthesized according to the method described in Example 1-6 of International Patent Publication No. WO 2017/038830.

Formula (9-1)

$$CF_3CF_2CF_2—O—(CF_2CF_2O)(CF_2CF_2O)\{(CF_2O)_{p9}(CF_2CF_2O)_{q9}\}—CF_2—CH_2OSO_2CF_3$$

Average value of p9: 22, average value of q9: 24

Synthesis Example 16: Synthesis of Compound (9-2)

$CuCl_2$ (7.0 mg), 1-phenyl-1-propyne (0.026 g), 1,3-bistrifluoromethylbenzene (15 mL), and compound (9-1) (4.03 g) were added, and then compound (B1-2) (4.0 mL, 1.0 M) was added. After stirring overnight at 50° C., the mixture was washed with 1 M hydrochloric acid and dried over sodium sulfate. After filtration, the solvent was removed by distillation and AC-6000 was added. After washing with methanol, flash column chromatography using silica gel was carried out to obtain 0.246 g of the following compound (9-2).

[Formula 39]

Compound (9-2)

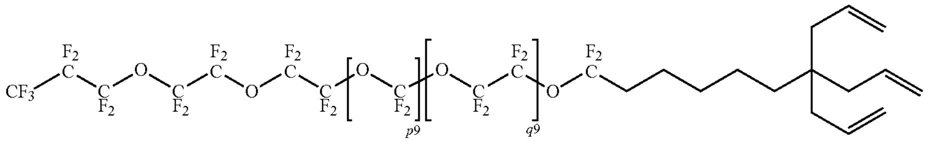

Average value of p9: 22, average value of q9: 24

NMR spectrum of compound (9-2):

1H-NMR (400 MHz, Chloroform-d) δ (ppm): 5.88-5.67 (m, 3H), 5.06-4.90 (m, 6H), 2.20-1.91 (m, 8H), 1.71-1.07 (m, 8H).

Example 22: Synthesis of Compound (IX)

AC-2000 (1.5 g), compound (9-2) (0.246 g), a solution of a platinum/1,3-divinyl-1,1,3,3-tetramethyl disiloxane complex (platinum content 2%, 3.9 mg) in xylene, aniline (1.1 mg), and trimethoxysilane (24.4 mg) were added, the mixture was stirred at 40° C. for 18 hours, and then the solvent was removed by distillation under reduced pressure to obtain 0.244 g of the following fluorine-containing ether compound (IX). The Mw/Mn of compound (IX) calculated by the GPC method was 1.10.

[Formula 41]

Formula (B-5)

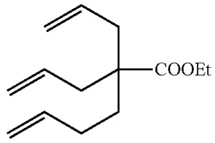

NMR spectrum of compound (B-5):

$^1$H-NMR (400 MHz, Chloroform-d) δ (ppm): 5.84-5.60 (m, 3H), 5.11-5.03 (m, 4H), 4.99 (dq, J=17.1, 1.6 Hz, 1H), 4.92 (ddt, J=10.1, 2.0, 1.2 Hz, 1H), 4.13 (q, J=7.1 Hz, 2H), 2.40-2.26 (m, 4H), 2.01-1.90 (m, 2H), 1.65-1.58 (m, 2H), 1.24 (t, J=7.1 Hz, 3H).

[Formula 40]

Compound (IX)

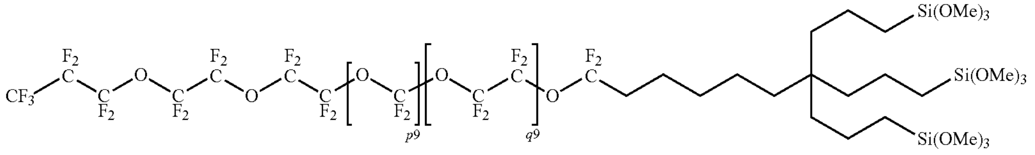

Average value of p9: 22, average value of q9: 24

NMR spectrum of compound (IX):

$^1$H-NMR (400 MHz, Chloroform-d) δ (ppm): 3.60 (s, 27H), 2.18-1.91 (m, 2H), 1.71-1.14 (m, 20H), 0.73-0.60 (m, 6H).

Synthesis Example 17: Synthesis of Compound (B-5)

THF (20 mL), diisopropylamine (4.2 mL) were added, the solution was then cooled to −78° C. A solution of n-butyl lithium in hexane (2.76 M, 9.9 mL) was added, and the temperature was raised to 0° C. After stirring, the solution was cooled to −78° C. to prepare a solution of lithium diisopropylamide (LDA) in THF. Compound (B-1) (4.00 g) was added to the THF solution, and after stirring, 4-bromo-1-butene (3.85 g) was added, and the mixture was stirred overnight at room temperature. After cooling to 0° C., 1 M hydrochloric acid (30 mL) was added, and THF was removed by distillation under reduced pressure. After extraction with dichloromethane, sodium sulfate was added. After filtration, the solvent was removed by distillation, and flash column chromatography using silica gel was carried out to obtain 4.01 g of compound (B-5).

Synthesis Example 18: Synthesis of Compound (B-6)

The compound (B-5) (4.01 g) was dissolved in THF (40 mL) and cooled to 0° C. A solution of lithium aluminum hydride in THF (27 mL) was added, and the mixture was stirred at 40° C. Water and an aqueous solution of 15% sodium hydroxide were added, and the mixture was stirred at room temperature. After filtration, the solvent was removed by distillation to obtain 2.41 g of the following compound (B-6).

[Formula 42]

Formula (B-6)

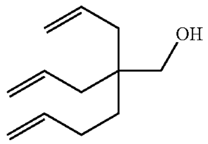

NMR spectrum of compound (B-5):

$^1$H-NMR (400 MHz, Chloroform-d) δ (ppm): 5.91-5.71 (m, 3H), 5.14-5.04 (m, 4H), 5.01 (dq, J=17.1, 1.6 Hz, 1H), 4.92 (ddt, J=10.1, 2.2, 1.2 Hz, 1H), 3.40 (d, J=6.2 Hz, 2H), 2.07-2.00 (m, 6H), 1.37-1.31 (m, 2H).

Example 23: Synthesis of Compound (B1-9)

Acetonitrile (7 mL), compound (B-6) (2.30 g), triphenylphosphine (3.61 g), and carbon tetrachloride (1.87 g) were added and stirred at 90° C. After concentration, ethyl acetate/hexane was added and the mixture was stirred. After filtration and concentration, distillation was carried out to obtain 1.85 g of the following compound (B1-9).

[Formula 43]

Formula (B1-9)

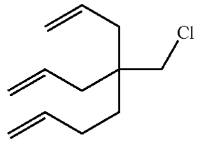

NMR spectrum of compound (B1-9):

$^1$H-NMR (400 MHz, Chloroform-d) δ (ppm): 5.87-5.66 (m, 3H), 5.15-5.06 (m, 4H), 5.01 (dq, J=17.1, 1.7 Hz, 1H), 4.94 (ddt, J=10.1, 1.9, 1.2 Hz, 1H), 3.35 (s, 2H), 2.11-1.98 (m, 6H), 1.42-1.31 (m, 2H).

Example 24: Synthesis of Compound (B2-9)

THF (3.8 mL) and iodine (0.031 g) were added to magnesium (0.182 g), and the mixture was stirred at room temperature. A solution of compound (B1-9) (1.12 g) in THF (3.8 mL) was added, and the mixture was heated to reflux for 2 hours to prepare a solution (0.8 M) of the following compound (B2-9).

[Formula 44]

Formula (B2-9)

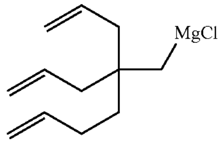

Synthesis Example 19: Synthesis of Compound (10-1)

$CuCl_2$ (16.0 mg), 1-phenyl-1-propyne (0.04 g), 1,3-bis-trifluoromethylbenzene (17 mL), and compound (1-2) (4.02 g) were added, and then compound (B2-9) (4.3 mL, 0.8 M) was added. After stirring at 50° C., the mixture was washed with 1 M hydrochloric acid and dried over sodium sulfate. After filtration, the solvent was removed by distillation and AC-6000 was added. After washing with MeOH, flash column chromatography using silica gel was carried out to obtain 0.35 g of the following compound (10-1).

[Formula 45]

Compound (10-1)

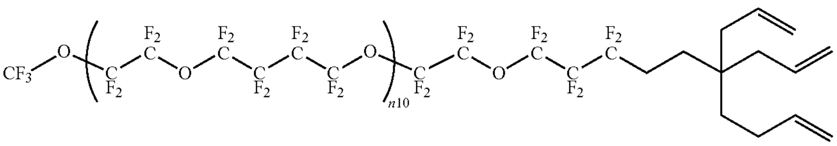

Average value (n10) of repeating units: 11

NMR spectrum of compound (B1-9):

$^1$H-NMR (400 MHz, Chloroform-d) δ (ppm): 5.84-5.66 (m, 3H), 5.12-4.81 (m, 6H), 2.19-1.90 (m, 8H), 1.60-1.51 (m, 2H), 1.33-1.26 (m, 2H).

$^{19}$F-NMR (376 MHz, Chloroform-d) δ (ppm): −55.09 (t, J=9.1 Hz), −81.95−−82.21 (m), −82.59, −87.4−−88.17 (m), −89.96 (q, J=9.0 Hz), −114.25, −124.99, −126.19.

Example 25: Synthesis of Compound (X)

AC-2000 (1.55 g), compound (10-1) (0.257 g), a solution of a platinum/1,3-divinyl-1,1,3,3-tetramethyl disiloxane complex (platinum content 2%, 9.9 mg) in xylene, aniline (7.4 mg), and trimethoxysilane (36.8 mg) were added, the mixture was stirred at 40° C., and then the solvent was removed by distillation under reduced pressure to obtain 0.253 g of the following fluorine-containing ether compound (X). The Mw/Mn of compound (X) calculated by the GPC method was 1.06.

[Formula 46]

Compound (X)

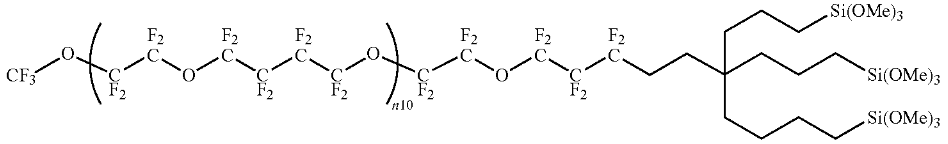

Average value (n10) of repeating units: 11

NMR spectrum of compound (X):

$^1$H-NMR (400 MHz, Chloroform-d) δ (ppm): 3.59 (d, J=2.0 Hz, 27H), 2.19-1.98 (m, 2H), 1.62-1.20 (m, 16H), 0.77-0.58 (m, 6H).

$^{19}$F-NMR (376 MHz, Chloroform-d) δ (ppm): −55.08 (t, J=9.2 Hz), −81.77-−82.86 (m), −87.43-−88.18 (m), −89.81-−90.18 (m), −113.67-−114.24 (m), −124.67-−125.10 (m), −125.81

Example 26: Synthesis of Compound (B1-10)

Acetonitrile (60 mL), 1,6-heptadien-4-ol (10.0 g), triphenylphosphine (30.6 g), carbon tetrachloride (16.0 g) were added and stirred at 90° C. After the reaction ended, distillation was carried out to obtain 1.86 g of compound (B1-10).

[Formula 47]

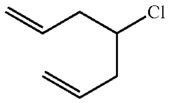

Formula (B1-10)

NMR spectrum of compound (B1-10):

$^1$H-NMR (400 MHz, Chloroform-d) δ (ppm): 5.84 (ddt, J=17.6, 9.7, 6.9 Hz, 2H), 5.18-5.05 (m, 4H), 3.94 (tt, J=7.4, 5.4 Hz, 1H), 2.59-2.36 (m, 4H).

Example 27: Synthesis of Compound (B2-10)

THF (6.5 mL) and iodine (36.0 mg) were added to magnesium (0.424 g) and the mixture was stirred at room temperature. A solution of compound (B1-10) (1.86 g) in THF (6.5 mL) was added, and the mixture was heated to reflux to prepare a solution (0.86 M) of the following compound (B2-10).

[Formula 48]

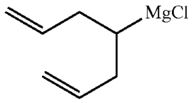

Formula (B2-10)

Example 28: Synthesis of Compound (B1-11)

1-Bromo-3-chloropropane (1.60 g), 1-phenyl-1-propyne (0.118 g), and $CuCl_2$ (0.027 g) were added and stirred at 0° C. The compound (B2-10) (0.86 M, 14.0 mL) was added, and the mixture was stirred. 1 M hydrochloric acid was added, extraction was carried out with dichloromethane, and sodium sulfate was added. After filtration and concentration, flash column chromatography using silica gel was carried out. Further, distillation was carried out to obtain 1.28 g of the following compound (B1-11).

[Formula 49]

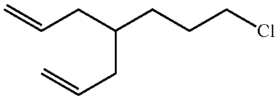

Formula (B1-11)

NMR spectrum of compound (B1-11):

$^1$H-NMR (400 MHz, Chloroform-d) δ (ppm): 5.84-5.66 (m, 2H), 5.09-4.96 (m, 4H), 3.51 (t, J=6.8 Hz, 2H), 2.15-2.01 (m, 4H), 1.86-1.71 (m, 2H), 1.59-1.47 (m, 1H), 1.45-1.35 (m, 2H).

Example 29: Synthesis of Compound (B2-11)

THF (4.5 mL) and iodine (39.0 mg) were added to magnesium (0.211 g) and the mixture was stirred at room temperature. A solution of compound (B1-11) (1.20 g) in THF (4.5 mL) was added, and the mixture was heated to reflux to prepare a solution (0.63 M) of the following compound (B2-11).

[Formula 50]

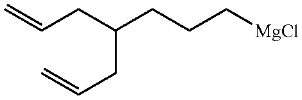

Formula (B2-11)

Synthesis Example 20: Synthesis of Compound (11-1)

$CuCl_2$ (27.0 mg), 1-phenyl-1-propyne (0.070 g), 1,3-bistrifluoromethylbenzene (29 mL), and compound (1-2) (4.30 g) were added, and then compound (B2-11) (9.5 mL, 0.63 M) was added. After stirring at room temperature, the mixture was washed with 1 M hydrochloric acid and dried over sodium sulfate. After filtration, the solvent was removed by distillation. Flash column chromatography using silica gel was then carried out to obtain 0.266 g of the following compound (11-1).

[Formula 51]

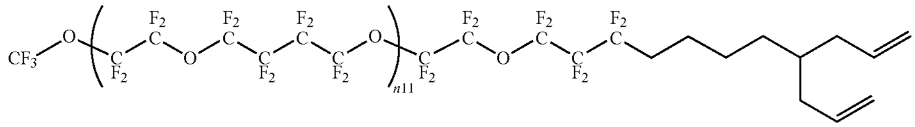

Compound (11-1)

Average value (n11) of repeating units: 13

Example 30: Synthesis of Compound (XI)

AC-2000 (1.55 g), compound (11-1) (0.257 g), a solution of a platinum/1,3-divinyl-1,1,3,3-tetramethyl disiloxane complex (platinum content 2%, 9.9 mg) in xylene, aniline (7.4 mg), and trimethoxysilane (36.8 mg) were added, the mixture was stirred at 40° C., and then the solvent was removed by distillation under reduced pressure to obtain 0.253 g of the following fluorine-containing ether compound (XI). The Mw/Mn of compound (XI) calculated by the GPC method was 1.07.

[Formula 52]

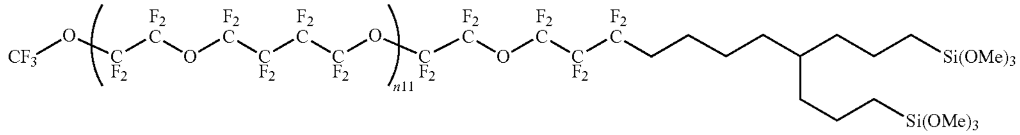

Compound (XI)

Average value (n11) of repeating units: 13

NMR spectrum of compound (XI):

$^1$H-NMR (400 MHz, Chloroform-d) δ (ppm): 5.72 (ddt, J=17.3, 10.2, 7.1 Hz, 2H), 5.06-4.84 (m, 4H), 2.18-1.88 (m, 6H), 1.66-1.14 (m, 7H).

$^{19}$F-NMR (376 MHz, Chloroform-d) δ (ppm): −56.65 (t, J=9.2 Hz), −83.60-−83.81 (m), −84.14, −89.06-−89.69 (m), −91.50 (q, J=9.0 Hz), −115.54, −126.56, −127.97.

Examples 31 to 41: Production and Evaluation of Article

Using the compounds I to XI, the substrate was surface treated to obtain the article of Examples 31 to 41. As the surface treatment method, in each example the following dry coating method and wet coating method each were performed. As the substrate, chemically strengthened glass was used. The obtained articles were evaluated based on the following methods. The results are shown in Table 1.

Dry Coating Method

The dry coating was carried out using a vacuum vapor deposition apparatus (manufactured by ULVAC Inc., VTR-350M) (vacuum vapor deposition method). 0.5 g of each compound was filled in a boat made of molybdenum in the vacuum vapor deposition apparatus, and the inside of the vacuum vapor deposition apparatus was evacuated to $1\times10^{-3}$ Pa or lower. The boat in which the compound had been placed was heated at a temperature increasing rate of 10° C./min or lower, and at the point when the vapor deposition rate by a quartz oscillator film thickness meter exceeded 1 nm/sec, the shutter was opened to start film deposition on the surface of the substrate. When the film thickness reached approximately 50 nm, the shutter was closed to end film deposition on the surface of the substrate. The substrate on which the compound had been deposited was heat treated at 200° C. for 30 minutes, and then washed with dichloropentafluoropropane (manufactured by AGC Inc., AK-225) to obtain an article having a surface layer on the surface of the substrate.

Wet Coating Method

Each compound obtained was mixed with $C_4F_9OC_2H_5$ (manufactured by 3M, Novec (register trade mark) 7200) as a medium to prepare a coating liquid having a solid content concentration of 0.05%. The substrate was dipped in the coating liquid, allowed to stand for 30 minutes, and then the substrate was taken out (dip coating method).

The coating film was dried at 200° C. for 30 minutes and washed with AK-225 to obtain an article having a surface layer on the surface of the substrate.

Evaluation Methods

Method for Measuring Contact Angle

The contact angle of approximately 2 μL of distilled water or n-hexadecane placed on the surface of the surface layer was measured using a contact angle measuring apparatus (manufactured by Kyowa Interface Science Co., Ltd., DM-500). Five different locations on the surface of the surface layer were measured, and the average value thereof was calculated. For the calculation of the contact angle, a 2θ method was employed.

Initial Contact Angle

The initial water contact angle and the initial n-hexadecane contact angle of the surface layer were measured by the above-described measurement method.

The evaluation criteria were as follows.

Initial water contact angle of fluorine-containing ether compound represented by formula (A1):

Circle (good): 115 degrees or more

Cross (poor): Less than 115 degrees

Initial water contact angle of fluorine-containing ether compound represented by formula (A2):

Circle (good): 115 degrees or more

Triangle (acceptable): 105 degrees or more and less than 115 degrees

Cross (poor): Less than 105 degrees

<Abrasion Resistance (Steel Wool)>

Steel wool Bon Star (#0000) was rubbed back-and-forth over the surface layer 10,000 times under a pressure of 98.07 kPa at a speed of 320 cm/min in accordance with JIS L0849: 2013 (ISO 105-X12: 2001) using a reciprocating traverse testing machine (manufactured by KNT), and then the water contact angle was measured by the method described above. The smaller the decrease in water repellency (water contact angle) after the rubbing is, the smaller the decrease in performance due to abrasion is, and the better the abrasion resistance is. The evaluation criteria were as follows.

Circle (good): Change in water contact angle after rubbing back-and-forth 10,000 times being 5 degrees or less Cross (poor): Change in water contact angle after rubbing back-and-forth 10,000 times being higher than 5 degrees Light Resistance The surface layer was irradiated with light beam (650 W/m$^2$, 300 to 700 nm) for 500 hours at a black panel temperature of 63° C. using a tabletop xenon arc lamp type accelerated light resistance testing machine (trade name: SUNTEST XLS+, manufactured by Toyo Seiki Seisaku-sho, Ltd.), and then the water contact angle was measured by the method described above. The evaluation criteria were as follows.

Circle (good): Change in water contact angle after the accelerated light resistance test being 5 degrees or less Cross (poor): Change in water contact angle after the accelerated light resistance test being higher than 5 degrees

TABLE 1

| | Example | 31 | 32 | 33 | 34 | 35 | 36 | 37 | 38 | 39 | 40 | 41 |
|---|---|---|---|---|---|---|---|---|---|---|---|---|
| Compound | Type | I | II | III | IV | V | VI | VII | VIII | IX | X | XI |
| Dry | Initial contact angle Water | ○ | ○ | ○ | ○ | ○ | ○ | ○ | Δ | ○ | ○ | ○ |
| Coating | Abrasion resistance | ○ | ○ | ○ | X | ○ | ○ | ○ | ○ | ○ | ○ | ○ |
| | Light resistance | ○ | ○ | ○ | X | ○ | ○ | ○ | ○ | ○ | ○ | ○ |
| Wet | Initial contact angle Water | ○ | ○ | ○ | ○ | ○ | ○ | ○ | Δ | ○ | ○ | ○ |
| coating | Abrasion resistance | ○ | ○ | ○ | X | ○ | ○ | ○ | ○ | ○ | ○ | ○ |
| | Light resistance | ○ | ○ | ○ | X | ○ | ○ | ○ | ○ | ○ | ○ | ○ |

As shown in Table 1, although the initial contact angle was good even for the compound IV, a decrease in the water contact angle after the abrasion test and the light resistance test was confirmed. On the other hand, the fluorine-containing ether compounds 1 to 111 and V to X1 that do not contain an ether bond (—C—O—C—) in the connecting group had a suppressed decrease in water contact angle even after abrasion test and light resistance test, and were shown to have excellent durability.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A fluorine-containing ether compound represented by the following formula (A1) or formula (A2):

Formula (A1)

$$R^f-O-(R^{f1}O)_m-R^{f2}[-R^1-C(-R^2-T)_a(-R^3)_{3-a}]_b,$$

Formula (A2)

$$[(T-R^2-)_a(R^3-)_{3-a}C-R^1-]_bR^{f2}-O-(R^{f1}O)_m-R^{f2}[-R^1-C(-R^2-T)_a(-R^3)_{3-a}]_b,$$

wherein $R^f$ is a fluoroalkyl group having 1 to 20 carbon atoms, $R^{f1}$ is a fluoroalkylene group having 1 to 6 carbon atoms, $R^{f2}$ is an organic group having a valence of (1+b), where at least a carbon atom bonded to $R^1$ bonds to a fluorine atom, and when there is a plurality of $R^{f2}$, the $R^{f2}$ may be the same or different, $R^1$ is an alkylene group having 5 to 20 carbon atoms, and when there is a plurality of $R^1$, the $R^1$ may be the same or different, $R^2$ is an alkylene group having 2 to 10 carbon atoms and optionally a fluorine atom, and a plurality of $R^2$ may be the same or different, $R^3$ is a hydrogen atom or an alkyl group having 1 to 10 carbon atoms and optionally a fluorine atom, and when there is a plurality of $R^3$, the plurality of $R^3$ may be the same or different, T is $-Si(R)_{3-c}(L)_c$, and a plurality of T may be the same or different, R is an alkyl group, L is a hydrolytic group or a hydroxyl group, and 2 or more L in T may be the same or different, m is an integer from 1 to 20, a is an integer from 1 to 3, and when there is a plurality of a, the plurality of a may be the same or different, b is an integer of 1 or more, and when there is a plurality of b, the plurality of b may be the same or different, c is 2 or 3, and a plurality of c may be the same or different, and when b is 1, a is 2 or 3, and wherein the fluorine-containing compound of formula (A1) or formula (A2) has a weight average molecular weight (Mw)/number average molecular weight (Mn) of 1.2 or less.

2. The fluorine-containing ether compound according to claim 1, wherein the number of $-CH_2-$ is from 8 to 30.

3. The fluorine-containing ether compound according to claim 1, wherein the hydrolytic group is an alkoxy group, an aryloxy group, a halogen atom, an acyl group, an acyloxy group, or an isocyanate group.

4. A surface treatment agent, comprising the fluorine-containing ether compound according to claim 1.

5. A fluorine-containing ether composition comprising: a fluorine-containing ether compound represented by the following formula (A1);

Formula (A1)

$$R^f—O—(R^{f1}O)_m—R^{f2}[—R^1—C(—R^2—T)_a(—R^3)_{3-a}]_b;$$

and a fluorine-containing ether compound represented by the following formula (A2);

Formula (A2)

$$[(T\text{-}R^2—)_a(R^3—)_{3-n}C—R^1—]_bR^{f2}—O—(R^{f1}O)_m—R^{f2}[—R^1—C(—R^2—T)_a(—R^3)_{3-a}]_b,$$

each according to claim 1.

6. A fluorine-containing ether composition comprising:

one or more of the fluorine-containing ether compound according to claim 1; and an additional fluorine-containing ether compound.

7. A coating liquid comprising:

the fluorine-containing ether compound according to claim 1; and a liquid medium.

8. A coating liquid comprising:

the fluorine-containing ether composition according to claim 6; and a liquid medium.

9. An article comprising a surface layer formed from the fluorine-containing ether compound according to claim 1 on a surface of a substrate.

10. An article comprising a surface layer formed from the fluorine-containing ether composition according to claim 5 on a surface of a substrate.

* * * * *